(12) United States Patent
Aranda Hernandez et al.

(10) Patent No.: US 11,793,411 B2
(45) Date of Patent: Oct. 24, 2023

(54) SENSING FOR HEART FAILURE MANAGEMENT

(71) Applicant: Medtronic, Inc., Minneapolis, MN (US)

(72) Inventors: Alfonso Aranda Hernandez, Maastricht (NL); Richard Cornelussen, Maastricht (NL); Mirko de Melis, Maastricht (NL); Richard Sutton, Monte Carlo (MC); Berthold Stegemann, Kassel (DE)

(73) Assignee: Medtronic, Inc., Minneapolis, MN (US)

( * ) Notice: Subject to any disclaimer, the term of this patent is extended or adjusted under 35 U.S.C. 154(b) by 420 days.

(21) Appl. No.: 16/797,390

(22) Filed: Feb. 21, 2020

(65) Prior Publication Data

US 2020/0345240 A1 Nov. 5, 2020

Related U.S. Application Data

(60) Provisional application No. 62/842,714, filed on May 3, 2019.

(51) Int. Cl.
*A61B 5/0205* (2006.01)
*A61B 5/07* (2006.01)
(Continued)

(52) U.S. Cl.
CPC .......... *A61B 5/0205* (2013.01); *A61B 5/076* (2013.01); *A61B 5/686* (2013.01); *A61B 5/6861* (2013.01);
(Continued)

(58) Field of Classification Search
CPC .......... A61B 2562/0219; A61B 5/0205; A61B 5/02405; A61B 5/076; A61B 5/0816;
(Continued)

(56) References Cited

U.S. PATENT DOCUMENTS 7,764,996 B2   7/2010   Zhang et al.
8,571,641 B2   10/2013   Kraemer et al.
(Continued)

OTHER PUBLICATIONS

International Search Report and Written Opinion of International Application No. PCT/US2020/024587, dated Jul. 13, 2020, 24 pp.
(Continued)

*Primary Examiner* — Jonathan T Kuo
*Assistant Examiner* — Vynn V Huh
(74) *Attorney, Agent, or Firm* — Shumaker & Sieffert, P.A.

(57) ABSTRACT

In some examples, determining a heart failure status using a medical device comprising one or more sensors includes determining a first value of a heart beat variability metric of a patient while an activity state of a patient satisfies an inactivity criterion based on a signal received from the one or more sensors, and determining, within a predetermined period of time after further determining that the activity state of the patient no longer satisfies the inactivity criterion, a second value of the heart beat variability metric while the activity state of the patient no longer satisfies the inactivity criterion based on the signal. A difference between the first value of the heart beat variability metric and the second value of the heart beat variability metric may be determined and the heart failure status of the patient may be determined based on the difference.

31 Claims, 9 Drawing Sheets

(51) Int. Cl.
| | |
|---|---|
| A61B 5/00 | (2006.01) |
| A61B 5/024 | (2006.01) |
| A61B 5/08 | (2006.01) |
| A61B 5/11 | (2006.01) |
| A61B 5/282 | (2021.01) |
| A61N 1/375 | (2006.01) |
| A61B 5/349 | (2021.01) |

(52) U.S. Cl.
CPC ........ *A61B 5/7282* (2013.01); *A61B 5/02405* (2013.01); *A61B 5/0816* (2013.01); *A61B 5/1116* (2013.01); *A61B 5/1118* (2013.01); *A61B 5/282* (2021.01); *A61N 1/3756* (2013.01)

(58) Field of Classification Search
CPC ..... A61B 5/1116; A61B 5/1118; A61B 5/282; A61B 5/349; A61B 5/686; A61B 5/6861; A61B 5/6869; A61B 5/7282; A61N 1/3756

See application file for complete search history.

(56) References Cited

U.S. PATENT DOCUMENTS

| | | | |
|---|---|---|---|
| 8,718,752 | B2 | 5/2014 | Libbus et al. |
| 8,790,257 | B2 | 7/2014 | Libbus et al. |
| 2008/0300449 | A1* | 12/2008 | Gerber ............... A61N 1/36007 600/30 |
| 2012/0253207 | A1 | 10/2012 | Sarkar et al. |
| 2013/0150912 | A1* | 6/2013 | Perschbacher ..... A61N 1/36592 607/18 |
| 2014/0107723 | A1* | 4/2014 | Hou ..................... A61N 1/3756 607/9 |
| 2014/0276928 | A1 | 9/2014 | Vanderpool et al. |
| 2015/0342540 | A1* | 12/2015 | An ....................... A61N 1/3702 600/483 |
| 2016/0038093 | A1 | 2/2016 | Sharma et al. |
| 2016/0310031 | A1 | 10/2016 | Sarkar |
| 2016/0367157 | A1* | 12/2016 | Blake ..................... A61B 5/053 |
| 2017/0001005 | A1 | 1/2017 | Zhang et al. |
| 2017/0231568 | A1 | 8/2017 | An et al. |
| 2018/0008204 | A1* | 1/2018 | An ....................... A61B 5/4836 |
| 2018/0035898 | A1 | 2/2018 | Gunderson |
| 2019/0069851 | A1 | 3/2019 | Sharma et al. |

OTHER PUBLICATIONS

Hinterseer et al., "Usefulness of Short-Term Variability of QT Intervals as a Predictor for Electrical Remodeling and Proarrhythmia in Patients With Nonischemic Heart Failure," The American Journal of Cardiology, vol. 106, No. 2, Jul. 15, 2010, pp. 216-220.

Cowie et al., "Development and Validation of an Integrated Diagnostic Algorithm Derived From Parameters Monitored in Implantable Devices for Identifying Patients at Risk for Heart Failure Hospitalization in an Ambulatory Setting," European Heart Journal, vol. 34, Aug. 14, 2013, pp. 2472-2480.

Kantelhardt et al., "Phase-Rectified Signal Averaging for the Detection of Quasi-Periodicities and the Prediction of Cardiovascular Risk," Chaos: An Interdisciplinary Journal of Nonlinear Science, vol. 17, No. 015112, Mar. 30, 2007, 10 pp.

* cited by examiner

SENSING FOR HEART FAILURE MANAGEMENT

This application claims the benefit of U.S. Provisional Patent Application Ser. No. 62/842,714, filed May 3, 2019, the entire content of which is incorporated herein by reference.

TECHNICAL FIELD

This disclosure relates generally to medical device systems, and, more particularly, medical device systems configured to monitor patient parameters.

BACKGROUND

Some types of medical devices may be used to monitor one or more physiological parameters of a patient, such as physiological parameters associated with cardiac function. Such medical devices may include, or may be part of a system that includes, sensors that detect signals associated with such physiological parameters; e.g., heart rate parameters. Values determined based on such signals may be used to assist in detecting changes in medical conditions, in evaluating the efficacy of a therapy, or in generally evaluating patient health.

Medical devices that monitor physiological parameters related to a medical condition of a patient may evaluate values associated with the physiological parameters, such as to determine whether the values exceed a threshold or have changed over time. Values that exceed a threshold or that have changed may indicate that a therapy being administered to the patient is not effectively managing the patient's medical condition.

SUMMARY

In general, this disclosure is directed to techniques for determining a heart failure status of a patient, such as a patient diagnosed with a heart failure condition. Such techniques may include performing assessments associated with aspects of a patient's cardiac function, such as determining a heart beat variability (HBV) metric, and determining the heart failure status of the patient based on the outcome of the assessments. Ongoing monitoring of aspects of the patient's cardiac function associated with a patient's condition (e.g., heart failure condition) may enable detection of changes in cardiac function before such changes lead to symptoms, acute decompensation, hospitalization and/or the progression or development of one or more medical conditions.

Some example techniques may include determining, by a medical device system including a medical device, a heart failure status of a patient based on at least one HBV metric, such as based on a difference between a first value of at least one HBV metric of the patient and a second value of the at least one HBV metric of the patient, or a comparison of a current value of at least one HBV metric of the patient to a baseline value of the at least one HBV metric. As an example, a first value of at least one HBV metric may be determined, based on at least one first signal received from one or more sensors (e.g., electrodes) of the medical device, while an activity state of the patient satisfies at least one inactivity criterion. The inactivity criterion may be a value of at least one of a patient activity level, a patient posture, a time of day, a patient heart rate, a patient respiration rate, or any other suitable criterion associated with a substantially inactive state of the patient. The second value of the at least one HBV metric may be determined, based on at least one second signal received from the one or more sensors, after determining the first value of the at least one HBV metric and while the activity state of the patient no longer satisfies the at least one inactivity criterion. Thus, the first value of the at least one HBV metric may be determined when the patient is substantially inactive (e.g., in a sleep state) and the second value of the at least one HBV metric may be determined when the patient is more active (e.g., in a waking state) than when the first value of the at least one HBV metric was determined. As discussed herein, determining a heart failure state of the patient based on changes in a value of at least one HBV metric associated with changes in an activity state of the patient may enable determination of a possibility that the patient will experience an adverse medical event and/or benefit from medical intervention.

The second value of the at least one HBV metric may be determined within a predetermined period of time after the activity state of the patient no longer satisfies the at least one inactivity criterion. For example, the second value of the at least one HBV metric may be determined within a predetermined period of time after patient activity has increased relative to a period of substantial patient inactivity (e.g., sleep) during which the first value of the at least one HBV metric was determined. A change in the at least one HBV metric occurring during the predetermined period of time, reflected by difference between the first value of the at least one HBV metric and the second value of the at least one HBV metric, may be indicative of the heart failure status of the patient.

Some other example techniques described herein may include determining a heart failure status of a patient based on a difference between a current value of at least one HBV metric and a baseline value of the at least one HBV metric. Such techniques may be used, for example, to monitor changes in an absolute value of the at least one HBV metric occurring during a particular portion of an activity cycle of a patient over the course of multiple activity cycles. An activity cycle of the patient may be a period of time in which the activity state of the patient both satisfies the at least one inactivity criterion subsequently no longer satisfies the at least one inactivity criterion, such as a period of one day. In some examples, monitoring changes in an absolute value of the at least one HBV metric occurring during a particular portion of an activity cycle of the over the course of multiple activity cycles may enable monitoring of different aspects of a heart failure status of the patient relative to monitoring changes in a difference between values of at least one HBV metric that occur during different portions of an activity cycle of the over the course of multiple activity cycles.

In any such examples, a value of a difference between first and second values of at least one HBV metric or a value of a difference between a current value of at least one HBV metric and a baseline value of the at least one HBV metric may be expected to be within a particular range in a patient who does not have a heart failure condition or who has a heart failure condition that is adequately compensated for by therapy. A determined value such a difference that is not within the range may be indicative of a developing or worsening heart failure condition. Thus, such a technique may include determining whether such a difference satisfies one or more HBV difference threshold values and/or one or more HBV threshold values. Determining the heart failure status of the patient further may include determining a possibility that the patient will experience an adverse medical event (e.g., worsening heart failure for which medical intervention may be beneficial) and/or transmitting the heart failure status of the patient to a remote computer for review by a clinician or other user.

In some other techniques, a clinician may determine the patient's heart failure status based on results of diagnostic or other evaluative procedures carried out during a clinician visit and prescribe treatment accordingly. For example, the clinician may prescribe medication and/or determine patient-specific values of one or more parameters at which a medical device may deliver electrical stimulation therapy (e.g., anti-arrhythmia pacing, cardiac resynchronization therapy (CRT), and/or other types of electrical stimulation therapy) to the patient's heart. However, the patient's treatment needs may change between clinician visits as the patient's heart-failure condition progresses or otherwise changes. Thus, ongoing monitoring of values of at least one HBV metric between clinician visits may enable early detection of changes in cardiac function before the changes lead to an adverse medical event such as recurrent symptoms, acute decompensation, and/or the progression or the patient's heart failure condition or development of one or more additional medical conditions.

Consequently, clinical outcomes may benefit from methods for determining a heart failure status of a patient based on determined values of at least one HBV metric of the patient between clinician visits, which in turn may enable early detection of heart failure progression and/or prediction of a possibility of hospitalization or other medical event. In response to such information, a patient's treatment may be adjusted (e.g., by modifying a drug regimen or values of one or more parameters at which a medical device may deliver electrical stimulation therapy). Prompt adjustment of one or more aspects of a patient's heart failure treatment as the patient's heart failure condition changes may help reduce the patient's possibility of acute decompensation, hospitalization, or development of additional medical conditions.

Accordingly, techniques described herein may enable periodic determination of a heart failure status of a patient between clinician visits. In some techniques described herein, a medical device system that includes a medical device may determine a patient's heart failure status and transmit the heart failure status to a remote computer or other device external to the patient. In some cases, the patient's heart failure status may indicate the patient's possibility of acute decompensation or hospitalization based on the heart failure. The remote computer then may transmit instructions for a medical intervention (e.g., instructions for changes to a drug regimen), to a user device used by the patient or a caregiver. In this manner, a patient's diagnoses and/or treatment for a heart failure condition may be modified as needed in between clinic visits, which may help avoid adverse medical events such as recurrent symptoms or hospitalization.

In one example, a method for determining a heart failure status of a patient using a medical device comprising one or more sensors comprises, by processing circuitry of a medical device system comprising the medical device, determining that an activity state of the patient satisfies at least one inactivity criterion based on at least one first signal received from the one or more sensors; determining a first value of at least one heart beat variability metric of the patient while the activity state of the patient satisfies the at least one inactivity criterion based on at least one second signal received from the one or more sensors, determining, after determining the first value of the at least one heart beat variability metric, that the activity state of the patient no longer satisfies the at least one inactivity criterion based on the at least one first signal, and determining, within a predetermined period of time after determining that the activity state of the patient no longer satisfies the at least one inactivity criterion, a second value of the at least one heart beat variability metric while the activity state of the patient no longer satisfies the at least one inactivity criterion based on the at least one second signal. The method further comprises determining a difference between the first value of the at least one heart beat variability metric and the second value of the at least one heart beat variability metric, and determining the heart failure status of the patient based on the difference.

In another example, a system for determining a heart failure status of a patient using a medical device comprises the medical device, wherein the medical device comprises one or more sensors, and processing circuitry. The processing circuitry is configured to determine that an activity state of the patient satisfies at least one inactivity criterion based on at least one first signal received from the one or more sensors, determine a first value of at least one heart beat variability metric of the patient while the activity state of the patient satisfies the at least one inactivity criterion based on at least one second signal received from the one or more sensors, determine, after determining the first value of the at least one heart beat variability metric, that the activity state of the patient no longer satisfies the at least one inactivity criterion based on the at least one first signal, and determine, within a predetermined period of time after determining that the activity state of the patient no longer satisfies the at least one inactivity criterion, a second value of the at least one heart beat variability metric while the activity state of the patient no longer satisfies the at least one inactivity criterion based on the at least one second signal. The processing circuitry is further configured to determine a difference between the first value of the at least one heart beat variability metric and the second value of the at least one heart beat variability metric, and determine the heart failure status of the patient based on the difference.

In another example, a non-transitory computer-readable medium stores instructions for causing processing circuitry to perform a method for determining a heart failure status of a patient using a medical device comprising one or more sensors, the method comprising, by processing circuitry of a medical device system comprising the medical device determining that an activity state of the patient satisfies at least one inactivity criterion based on at least one first signal received from the one or more sensors, determining a first value of at least one heart beat variability metric of the patient while the activity state of the patient satisfies the at least one inactivity criterion based on at least one second signal received from the one or more sensors, determining, after determining the first value of the at least one heart beat variability metric, that the activity state of the patient no longer satisfies the at least one inactivity criterion based on the at least one first signal, and determining, within a predetermined period of time after determining that the activity state of the patient no longer satisfies the at least one inactivity criterion, a second value of the at least one heart beat variability metric while the activity state of the patient no longer satisfies the at least one inactivity criterion based on the at least one second signal. The method further comprises determining a difference between the first value of the at least one heart beat variability metric and the second value of the at least one heart beat variability metric, and determining the heart failure status of the patient based on the difference.

In another example, a method for determining a heart failure status of a patient using a medical device comprising one or more sensors comprises, by processing circuitry of a medical device system comprising the medical device, determining that an activity state of the patient satisfies at least one inactivity criterion based on at least one first signal received from the one or more sensors, determining that the activity state of the patient has increased by determining that the activity state of the patient no longer satisfies the at least one inactivity criterion based on the at least one first signal after determining that the activity state of the patient satisfies the at least one inactivity criterion, and determining, within a predetermined period of time after determining that the activity state of the patient has increased, a current value of at least one heart beat variability metric while the activity state of the patient no longer satisfies the at least one the inactivity criterion based on at least one second signal received from the one or more sensors. The method further comprises comparing the current value of the at least one heart beat variability metric to a baseline value of the at least one heart beat variability metric, and determining the heart failure status of the patient based on the comparison.

In another example, a system for determining a heart failure status of a patient using a medical device comprises the medical device, wherein the medical device comprises one or more sensors, and processing circuitry. The processing circuitry is configured to determine that an activity state of the patient satisfies at least one inactivity criterion based on at least one first signal received from the one or more sensors, determine that the activity state of the patient has increased by determining that the activity state of the patient no longer satisfies the at least one inactivity criterion based on the at least one first signal after determining that the activity state of the patient satisfies the at least one inactivity criterion, and determine, within a predetermined period of time after determining that the activity state of the patient has increased, a current value of at least one heart beat variability metric while the activity state of the patient no longer satisfies the at least one the inactivity criterion based on at least one second signal received from the one or more sensors. The processing circuitry is further configured to compare the current value of the at least one heart beat variability metric to a baseline value of the at least one heart beat variability metric, and determine the heart failure status of the patient based on the comparison.

In another example, a non-transitory computer-readable medium storing instructions for causing processing circuitry to perform a method for determining a heart failure status of a patient using a medical device comprising one or more sensors, the method comprising, by processing circuitry of a medical device system comprising the medical device determining that an activity state of the patient satisfies at least one inactivity criterion based on at least one first signal received from the one or more sensors, determining that the activity state of the patient has increased by determining that the activity state of the patient no longer satisfies the at least one inactivity criterion based on the at least one first signal after determining that the activity state of the patient satisfies the at least one inactivity criterion, and determining, within a predetermined period of time after determining that the activity state of the patient has increased, a current value of at least one heart beat variability metric while the activity state of the patient no longer satisfies the at least one the inactivity criterion based on at least one second signal received from the one or more sensors. The method further comprises comparing the current value of the at least one heart beat variability metric to a baseline value of the at least one heart beat variability metric, and determining the heart failure status of the patient based on the comparison.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below. Other features, objects, and advantages of this disclosure will be apparent from the description and drawings, and from the claims.

DETAILED DESCRIPTION

Figure 1:
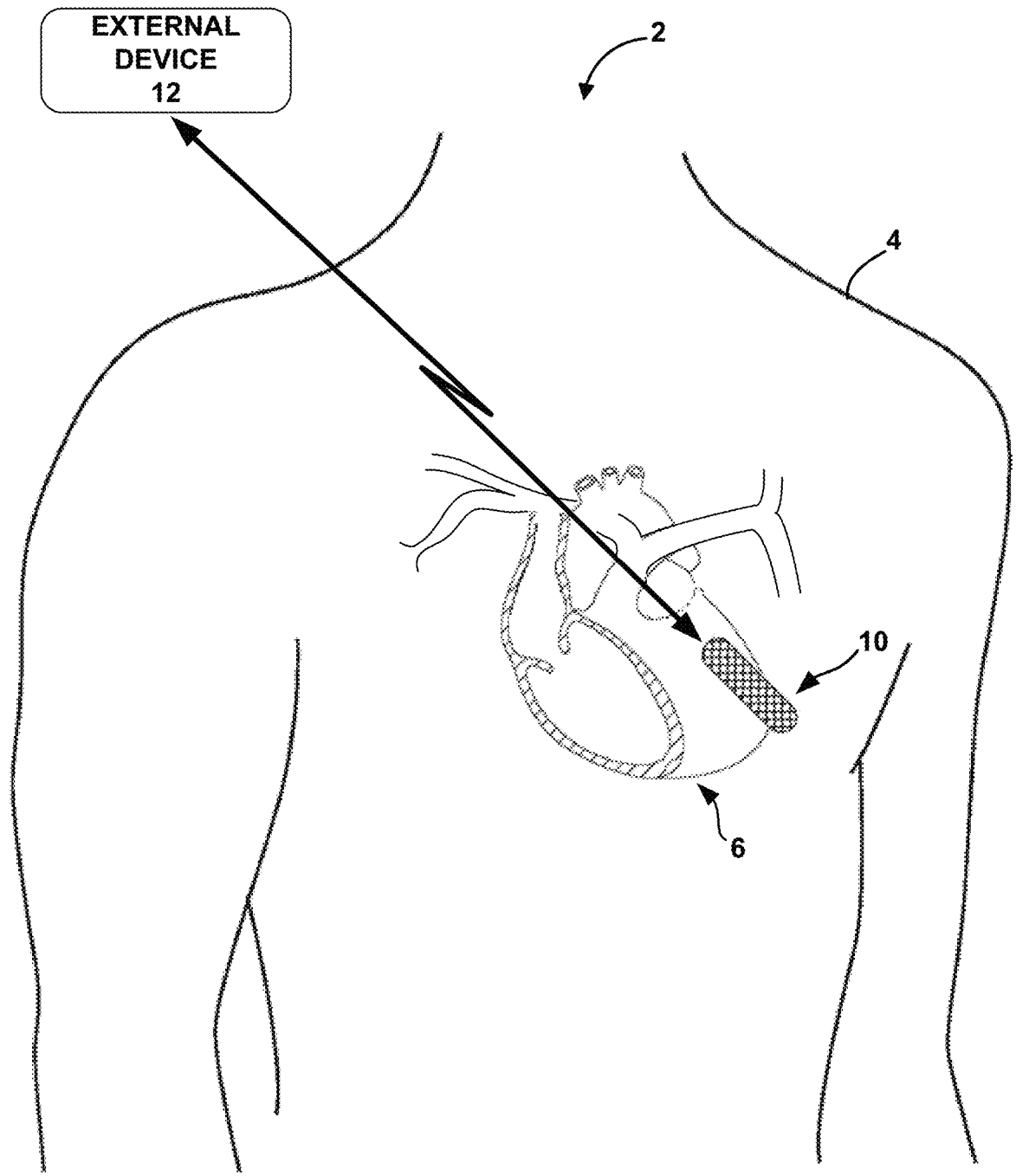
FIG. 1 is a conceptual drawing illustrating an example of a medical device system including a leadless implantable medical device and an external device in conjunction with a patient.

In general, this disclosure describes example techniques and systems related to determining a heart failure status of a patient based on values of one or more HBV metrics associated with cardiac function of the patient and determined during one or more particular activity states of the patient. Processing circuitry of a medical device comprising one or more sensors (e.g., one or more electrodes, accelerometers, or other sensors), or a system that includes the medical device, may determine that an activity state of the patient satisfies at least one inactivity criterion based on at least one first signal received from the one or more sensors. For example, the processing circuitry may determine that the activity state of the patient satisfies the at least one inactivity criterion by determining that a value of at least one of a patient activity level, a patient posture, a time of day, a patient heart rate, or a patient respiration rate is indicative of patient inactivity and/or sleep. In examples in which the at least one inactivity criterion includes a time of day, the processing circuitry may be configured to account for changes in time that may occur, such as when the patient travels from one time zone to another time zone and/or when daylight-savings time begins or ends. As described herein, changes in values of one or more HBV metrics that occur with changes in an activity state, such as an increase in an activity level of the patient, may be associated with a heart failure status of the patient.

While the activity state of the patient satisfies the at least one inactivity criterion, the processing circuitry may determine a first value of at least one HBV metric of the patient based on at least one second signal received from the one or more sensors, which may comprise a plurality of electrodes. In such examples, the at least one second signal may be a cardiac electrogram signal received from at least two of the plurality of electrodes. In some examples, the at least one inactivity criterion may be associated with a sleep state of the patient. Thus, in some examples, the first value of the at least one HBV metric that the processing circuitry determines during the predetermined period of time may be a sleeping value of the at least one HBV metric.

The processing circuitry may determine, after determining the first value of the at least one HBV metric, that the patient activity state no longer satisfies the at least one patient inactivity criterion. A change in the patient activity state such that the patient activity state no longer satisfies the at least one patient inactivity criterion may be associated with the patient awakening from sleep or otherwise increasing his or her activity level. Within a predetermined period of time after determining that the activity state of the patient no longer satisfies the at least one inactivity criterion and while the activity state of the patient no longer satisfies the at least one inactivity criterion, the processing circuitry may determine a second value of the at least one HBV metric based on the at least one second signal. In examples in which the at least one inactivity criterion is associated with a sleep state of the patient, the processing circuitry may determine that the patient activity state no longer satisfies the at least one patient inactivity criterion when the patient activity state has no longer satisfied the at least one patient inactivity criterion for a period of time that satisfies an associated threshold value. In some such examples, the threshold value may be associated with the patient being likely to have awakened for the day or another relatively extended duration, rather than only briefly awakening and then returning to a sleep state. In some such examples, it may be desirable to exclude instances in which the patient only briefly awakens from characterization as the patient no longer being in a sleep state at least because changes in a value of at least one HBV metric of interest may not occur within the predetermined period of time after such brief waking periods.

The predetermined period of time may be associated with a period of time, after the activity state of the patient changes from satisfying at least one inactivity criterion to no longer satisfying the at least one inactivity criterion, during which changes in the value of the at least one HBV metric associated with changes in activity state are expected to occur. For example, the predetermined period of time may be a period of time after the patient has awakened from a sleep state. Thus, in some examples, the second value of the at least one HBV metric that the processing circuitry determines during the predetermined period of time may be a waking value of the at least one HBV metric. In some examples, the predetermined period of time may be about 30 minutes, such as about 15-30 minutes.

In some examples, the processing circuitry may determine, prior to determining that the activity state of the patient no longer satisfies the at least one inactivity criterion, that a period of time during which the activity state of the patient is expected to satisfy the at least one inactivity criterion has elapsed. Such a period of time may be associated with a period of time during which the patient is expected to be asleep or during which the activity state of the patient otherwise is expected to satisfy at least one inactivity criterion, and the expiration of such a period of time may be associated with a time at which the patient is expected to awaken or during which the activity state of the patient otherwise is expected to no longer satisfy the at least one inactivity criterion. The period of time may be adapted, e.g., automatically or based on user programming, to the patient's habits, such as a habitual sleep/wake schedule. Based on the determination that the period of time during which the activity state of the patient is expected to satisfy the at least one activity criterion has elapsed, the processing circuitry may increase a frequency at which an activity state of the patient is determined in order to identify or approximate the time at which the activity state of the patient ceases to satisfy the at least one inactivity criterion (e.g., awakens from a sleep state and arises). Identifying or approximating the time at which the activity state of the patient ceases to satisfy the at least one inactivity criterion may enable the processing circuitry to identify or approximate the beginning of the predetermined period of time and determine the second value of the at least one HBV metric within the predetermined period of time.

In any such examples, the processing circuitry may determine a difference between the first value of the at least one HBV metric and the second value of the at least one HBV metric and determine the heart failure status of the patient based on the difference. The processing circuitry may determine the heart failure status of the patient based on the difference by determining whether the difference satisfies an HBV difference threshold value that is associated with a change in the heart failure status of the patient.

The HBV threshold difference value may be associated with a lower end or a higher end of an HBV difference range. An HBV difference range may represent a range of values of the difference between the first and second values of the at least one HBV metric that are associated with a baseline heart failure status of the patient (e.g., a state in which a heart failure condition of the patient is adequately compensated and/or stable). A value near the lower end of such a range may be associated with a different heart failure status of the patient than a value near the higher end of such a range. For example, a value of the difference between the first and second values of the HBV metric that satisfies a threshold value associated with a higher end of the HBV difference range may be indicative of worsening heart failure and/or increasing risk of tachyarrhythmia or bradyarrhythmia. Thus, in some examples, the techniques for determining a heart failure status of a patient described herein may include determining a status of one or more other aspects of cardiac function of the patient, such as an arrhythmia-prone status of the patient. A value of the difference between the first and second values of the HBV metric that does not satisfy a threshold value associated with a lower end of the HBV difference range may be indicative of an advanced state of heart failure. Thus, in some examples, determining a heart failure status of the patient may include comparing the difference between the first and second values of the at least one HBV metric to more than one HBV threshold difference value.

In some examples, an HBV threshold difference value may be a patient-specific HBV threshold difference value. The patient-specific HBV threshold difference value may be periodically updated, such as to track trends in the difference between the first and second values of the at least one HBV metric over multiple activity cycles of the patient. An activity cycle of the patient may be a period of time in which the processing circuitry both determines that the activity state of the patient satisfies the at least one inactivity criterion and determines that the activity state of the patient no longer satisfies the at least one inactivity criterion, such as a period of one day. In some such examples, the HBV difference threshold value may be based on one or more values of the difference between the first and second values of the at least one HBV metric that correspond to one or more previous activity cycles of the patient.

The processing circuitry may update the HBV difference threshold value based on a determination that a predetermined number of activity cycles have elapsed. For example, if the processing circuitry determines that values of the difference between the first and second values of the at least one HBV metric is trending upward or downward over one or more past activity cycles (e.g., days), the processing circuitry may update the HBV difference threshold by modifying the HBV difference threshold value. For example, the processing circuitry may lower HBV threshold difference value that is associated with a lower end of an HBV difference range if the difference between the first and second values of the at least one HBV metric is trending downward, thereby increasing the significance of any further decrease in the difference between the first and second values of the at least one HBV metric that may occur in subsequent activity cycles.

In some other examples, instead of determining a heart failure status of the patient based on the difference between the first and second values of the at least one HBV metric, the processing circuitry may be configured to determine the heart failure status of a patient by determining a current value of at least one HBV metric while the activity state of the patient no longer satisfies the at least one the inactivity criterion, comparing the current value of the at least one HBV metric to a baseline value of the at least one HBV metric, and determining the heart failure status of the patient based on the comparison. In some such examples, the processing circuitry may compare the current value of the at least one HBV metric to the baseline value of the at least one HBV metric by determining whether a difference between the current value of the at least one HBV metric and the baseline value of the at least one HBV metric satisfies at least one corresponding HBV threshold value that is associated with a change in the heart failure status of the patient. However, other aspects of such example techniques may be substantially similar to corresponding aspects of example techniques in which the processing circuitry is configured to determine the heart failure status of the patient based on the difference between the first and second values of the at least one HBV metric.

In some examples, the medical device may be an implantable medical device (IMD) configured for implantation within the patient. The IMD may include a housing, configured for subcutaneous implantation, on which the one or more sensors are positioned. In some examples, the IMD may be a leadless 1 MB. In other examples, the medical device may be one or more other implanted or external devices or servers. Examples of the one or more other implanted or external devices may include an implanted, multi-channel cardiac pacemaker, implantable cardioverter-defibrillator (ICD), implantable pulse generator (IPG), leadless (e.g., intracardiac) pacemaker, extravascular pacemaker and/or ICD, or other 1 MB or combination of such IMDs, an external monitor, or a drug pump.

In any such examples, the processing circuitry may transmit the heart failure status of the patient to a remote computer, receive instructions from the remote computer for a medical intervention based on the heart failure status of the patient, and transmit the instructions for the medical intervention to a user interface. Such instructions for a medical intervention may include at least one of a change in a drug selection, a change in a drug dosage, instructions to schedule a visit with a clinician, or instructions for the patient to seek medical attention. In this manner, a patient's diagnoses and/or treatment for a heart failure condition may be modified as needed in between clinic visits, which may help avoid adverse medical events such as recurrent symptoms, acute decompensation, or hospitalization.

Although a heart failure status of a patient may be determined based on results of diagnostic or other evaluative procedures (e.g., examination of a cardiac electrogram, blood tests, stress tests, or others), such other techniques for determining heart failure status may require a clinician visit and thus may only be performed infrequently, such as at intervals of one or more weeks or months. Thus, such other techniques may not enable early detection of changes in such physiological functions before the changes lead to adverse medical events.

Changes in values of the at least one HBV metric associated with changes in patient activity, such as changes that occur soon after the patient awakens from a sleep state, may provide information regarding the heart failure status of the patient not provided by other techniques. For example, a patient's vascular tone may be expected to increase within about 30 minutes after awakening and arising. The increase in vascular tone may reflect higher epinephrine blood levels, which may precipitate adverse medical events. Studies on circadian patterns suggest that changes in vascular tone occurring during the period of about 30 minutes after an increase in patient activity (e.g., after awakening) may reflect changes in the balance between sympathetic activity and vagal tone) and may be identified based on changes in values of at least one HBV metric. Changes in the balance between sympathetic activity and vagal tone, occurring either during one activity cycle or across multiple activity cycles, may be associated with changes in a heart failure condition of the patient. Although monitoring changes in values of at least one HBV metric associated with changes in patient activity thus may enable accurate and/or efficient monitoring of changes in a heart failure status of a patient, such techniques may not readily be carried out during clinician visits. For example, it may be impractical to monitor values of at least one HBV metric for a period of time encompassing both an activity state of the patient that satisfies at least one inactivity criterion and an activity state of the patient that no longer satisfies the at least one inactivity criterion.

In some examples, the techniques described herein may enable identification of changes in a heart failure status of a patient before the changes lead to symptoms, acute decompensation, and/or the progression or the patient's heart failure condition or development of one or more additional medical conditions. Thus, the techniques described herein may help enable determination of possibility that the patient will experience an adverse medical event, which may help clinicians prescribe personalized treatment to help avert hospitalizations, improve clinical outcomes, and/or reduce the economic burden on the health care system.

FIG. 1 illustrates the environment of an example medical device system 2 in conjunction with a patient 4 and a heart 6, in accordance with an apparatus and method of certain examples described herein. The example techniques may be used with an IMD 10, which may be leadless and in wireless communication with external device 12, as illustrated in FIG. 1. In some examples, IMD 10 may be coupled to one or more leads. In some examples, IMD 10 may be implanted outside of a thoracic cavity of patient 4 (e.g., subcutaneously in the pectoral location illustrated in FIG. 1). IMD 10 may be positioned near the sternum near and/or just below the level of heart 6.

In some examples, IMD 10 may take the form of a Reveal LINQ™ Insertable Cardiac Monitor (ICM), available from Medtronic plc, of Dublin, Ireland. External device 12 may be a computing device configured for use in settings such as a home, clinic, or hospital, and may further be configured to communicate with IMD 10 via wireless telemetry. For example, external device 12 may be coupled to a remote patient monitoring system, such as Carelink®, available from Medtronic plc, of Dublin, Ireland. External device 12 may, in some examples, comprise a programmer, an external monitor, or a consumer device such as a smart phone or tablet. In other examples, the example techniques and systems described herein may be used with an external medical device in addition to, or instead of IMD 10. Such an external medical device may be positioned externally to patient 4 (e.g., positioned on the skin of patient 4) and may carry out any or all of the functions described herein with respect to IMD 10.

Medical device system 2 may include one or more sensors (e.g., for sensing an activity state of patient 4 and/or cardiac function of patient 4). The one or more sensors collectively may detect at least one first signal and at least one second signal that enable a processing circuitry of medical device system 2 to determine whether an activity state of patient 4 satisfies at least one inactivity criterion and determine values of at least one HBV metric based on such signals. Although such processing circuitry may be contained within IMD 10 and/or within another medical device of medical device system 2, e.g., external device 12, the processing circuitry may be described herein as being a component of IMD 10 for the sake of clarity.

In some examples, the one or more sensors may include one or more accelerometers or other sensors configured to detect the at least one first signal, which may be at least one signal indicative of one or more aspects of an activity state of patient 4, such as activity level, posture, and/or respiration rate. As discussed in further detail below with respect to FIGS. 3-4B, such one or more accelerometers may be enclosed within a housing of IMD 10. The one or more accelerometers may comprise one or more three-axis accelerometers and may be a component of IMD 10 or a component of another medical device of medical device system 2. Signals generated by such sensors may be indicative of whether an activity state of patient 4 satisfies at least one inactivity criterion, such as patient activity level, patient posture (e.g., lying down or upright), or a patient respiration rate.

In some examples, the one or more sensors may include a plurality of electrodes, which may be positioned on the housing of IMD 10. The plurality of electrodes may be configured to detect the at least one second signal, which may be a cardiac electrogram. The processing circuitry may determine the values of the at least one HBV metric based on the at least one second signal. An HBV metric may be a measure of variability within a set of values of a parameter of patient 4 collected during a measurement period, on which basis the processing circuitry may determine the value of the HBV metric of patient 4. For example, the processing circuitry may determine a first, second, current, baseline, or other value of an HBV metric of patient 4 by determining a difference between each value and a subsequent value collected during the measurement period and averaging or otherwise analyzing the differences to determine the value of the HBV metric of patient 4. In some examples, the HBV metric may be a corresponding at least one of a T-wave alternans metric, a PR duration metric, a short-term variability metric, or a phase-rectified signal averaging metric, based on the at least one second signal received from the plurality of electrodes. One or more such HBV metrics also may be a heart rate variability (HRV) metric, such as a PR duration or a short-term variability metric, although in other examples such HBV metrics may not necessarily be an HRV metric.

The processing circuitry may determine a difference between a first value of the at least one HBV metric determined while the activity state of patient 4 satisfies at least one inactivity criterion and a second value of the at least one HBV metric determined while the activity state of patient 4 no longer satisfies the inactivity criterion. In some examples, the processing circuitry may determine a difference between a current value of at least one HBV metric determined after determining an activity state of patient 4 has increased and a baseline value of the at least one HBV metric. The processing circuitry then may determine a heart failure status of patient 4 based on the difference between the first and second values of the at least one HBV metric or the comparison of the current value of the at least one HBV metric and the baseline value of the at least one HBV metric.

In any such examples, processing circuitry of medical device system 2 may transmit a determined heart failure status of patient 4 to a remote computer (e.g., external device 12). The processing circuitry then may receive instructions for a medical intervention from the remote computer based on the heart failure status of patient 4 and transmit the instructions for the medical intervention to a user interface.

In some examples, an interval at which processing circuitry of medical device system 2 determines a heart failure status of patient 4 is the same as an interval at which the processing circuitry transmits the heart failure status to a remote computer. In other examples, the processing circuitry may determine a heart failure status of patient 4 more frequently than the processing circuitry transmits a heart failure status to the remote computer. By determining a heart failure status more often than a heart failure status is transmitted, an accuracy of a technique for determining a heart failure status may be enhanced by eliminating outlier measurements. For example, the processing circuitry may determine that a difference between first and second values of at least one HBV metric or a difference between a current value of at least one HBV metric and a corresponding baseline value of the at least one HBV metric satisfies a threshold only if a certain number or proportion of preceding results satisfied the threshold. In other examples, a single incident in which such a difference satisfied a threshold may suffice to cause the processing circuitry to determine that a change in the heart failure status of patient 4 has occurred.

In some examples, a clinician may configure a sensitivity of the processing circuitry to different threshold values at or after the time of implant of IMD 10, depending on factors such as the individual condition of patient 4 (e.g., a medical history of patient 4) and/or clinical data for a patient population having one or more characteristics in common with patient 4. For example, a clinician may configure a sensitivity of the processing circuitry based on a stage of a heart failure condition of patient 4 and/or an arrhythmia history of patient 4. In examples in which a technique includes comparing a difference between first and second values of at least one HBV metric or a difference between a current value of at least one HBV metric an d a corresponding baseline value to more than one threshold value (e.g., a first threshold value associated with a lower end of a range and a second threshold value associated with a lower end of a range), a clinician may configure the processing circuitry to be more sensitive to values that satisfy the first threshold value. For example, the processing circuitry may determine that the heart failure status of patient 4 has changed if a difference between first and second values of at least one HBV metric or a difference between a current value of at least one HBV metric and a corresponding baseline value satisfies one of the first threshold value or the second threshold value fewer times than may be required for the other threshold value, such as depending on which threshold, if satisfied, may be more predictive of an adverse medical event for patient 4. As discussed below, several aspects of the operation of IMD 10 may be configured by a clinician to help achieve improved monitoring and clinical outcomes for individual patients such as patient 4.

In some examples, a clinician may configure the processing circuitry to utilize different threshold values or otherwise adjust the sensitivity of the detection of the heart failure status based on one or more other criteria, such as an occupational schedule of patient 4 in examples in which patient 4 is engaged in an occupation. For example, changes in a heart failure status of patient 4 may be more likely to occur during workdays than during non-workdays. In some examples, changes in a heart failure status of patient 4 may be more likely to occur on a first day of a period of multiple workdays (e.g., a first workday of a workweek). This phenomenon may be associated with increases in stress levels and/or physical exertion experienced by patient 4 on workdays relative to non-workdays and on a first workday of a workweek relative to subsequent workdays. In some such examples, a clinician may configure a sensitivity with which the processing circuitry identifies changes in heart failure status by setting one or more threshold values for a workday of patient 4 that differ from one or more corresponding threshold values non-workdays of patient 4 and/or from other workdays of a period of multiple workdays. Additionally, or alternatively, the clinician may configure the processing circuitry to be more sensitive to values that satisfy a first threshold value than values that satisfy a second threshold value, or vice versa, on workdays (i.e., workdays in general or a particular workday) of patient 4 than on non-workdays or other workdays of patient 4. In this manner, the sensitivity of processing circuitry of IMD 10 may be adapted to account for times when a heart failure status of patient 4 may be more likely to change.

In some examples, IMD 10 may be configured to undertake a learning phase after implantation into patient 4. During such a learning phase, the processing circuitry may determine one or more baseline values and one or more threshold values, which the processing circuitry may store in a memory of IMD 10 or other device of medical device system 2. For example, the processing circuitry may determine a baseline difference between a first value of the at least one HBV metric determined while the activity state of patient 4 satisfies at least one inactivity criterion (e.g., during a sleep state) and a second value of the at least one HBV metric determined while the activity state of patient 4 no longer satisfies the inactivity criterion (e.g., soon after waking). For example, IMD 10 may determine differences between the first and second values of the at least one HBV metric during a plurality of activity cycles over a period of time (e.g., a week or more) to determine a baseline difference value during a period when the condition of patient 4 is stable and not decompensating. In some examples, the processing circuitry may determine the baseline difference value by averaging or otherwise combining the differences between the first and second values of the at least one HBV metric during the plurality of activity cycles of patient 4. Based on the determined baseline difference value between the first and second values of the at least one HBV metric, the processing circuitry or a clinician may determine an HBV difference threshold value. An HBV difference threshold value may be an HBV difference value that is greater than or less than the baseline difference value by a predetermined amount indicative of a change in the heart failure status of patient 4.

In examples in which the processing circuitry determines the heart failure status of patient 4 based on a difference between a current value of at least one HBV metric determined within a predetermined period of time after determining that an activity state of patient 4 has increased (e.g., soon after waking) and a corresponding baseline value, the processing circuitry similarly may determine the baseline value of the at least one HBV metric during a plurality of activity cycles. In such examples, the processing circuitry or a clinician may determine an HBV threshold value, which may be an HBV value that is greater than or less than the baseline difference value by a predetermined amount indicative of a change in the heart failure status of patient 4. In some examples, the processing circuitry may determine the baseline difference value by averaging or otherwise combining the differences between the first and second values of the at least one HBV metric during the plurality of activity cycles of patient 4.

In any such examples, the processing circuitry may determine the baseline values by averaging values collected during the training period, although the processing circuitry may use other methods of determining baseline values from collected values. In some examples, the processing circuitry may reject outlier values collected during the training period prior to determining the baseline values based on the remaining collected values. In this manner, a baseline value of at least one HBV metric may be based on a relatively large group of past values of the at least one HBV metric of patient 4. In some examples, the processing circuitry may determine values of at least one HBV metric of patient 4 that are compared corresponding baseline value, either directly or by comparison to a threshold value based on a baseline value, based on a relatively smaller group of values of the at least one HBV metric. For example, the processing circuitry may determine a first value, a second value, and/or a current value of at least one HBV metric of patient 4 based on a short-term average of a relatively smaller group of recent values of the at least one HBV metric occurring subsequent to the activity cycles on which a corresponding baseline value is based. Thus, in some examples, the processing circuitry may determine one or more values of an HBV metric by averaging or otherwise combining a group of such values.

Because heart failure conditions may be progressive in nature, baseline and/or threshold values associated with patient 4 may be updated periodically. For example, IMD 10 may undertake a new learning phase monthly, quarterly, yearly, or at an expiration of any other appropriate period. The new learning phase may produce new values associated with one or more baseline and/or threshold values described with respect to the techniques described herein, based on an updated heart failure status of patient 4. In other examples, a clinician may program IMD 10 to update such values as needed, such as following a health event experienced by patient 4 that may affect the applicability of such values to one or more aspects of the heart failure status of patient 4.

In addition to or instead of undertaking a new learning phase to determine one or more updated threshold values, the processing circuitry may determine one or more threshold values based on trends in determined values of one or more HBV metrics of patient 4. Determining one or more threshold values based on such trends may help enable detection of additional aspects of changes in a heart failure state of patient 4. As discussed above, a difference between first and second values of at least one HBV metric or a difference between current and baseline values of at least one HBV metric that satisfies a threshold value associated with a higher end of an HBV difference range may be indicative of worsening heart failure and/or increasing risk of tachyarrhythmia or bradyarrhythmia, whereas such a difference that does not satisfy a threshold value associated with a lower end of an HBV difference range may be indicative of an advanced state of heart failure. However, fluctuations in such differences that satisfy a threshold value associated with a lower end of an HBV difference range and do not satisfy a threshold value associated with a higher end of an HBV difference range nonetheless may be indicative of changes in heart failure status.

For example, an increase in an absolute value of such fluctuations across one or more previous activity cycles of patient 4 may be indicative of increasingly irregular cardiac function of patient 4. Additionally, or alternatively, fluctuations in such differences that occasionally do not satisfy a threshold value associated with a lower end of an HBV difference range or that occasionally satisfy a threshold value associated with a higher end of an HBV difference range may be indicative of increasingly irregular cardiac function of patient 4. Increasingly irregular cardiac function, which may be associated with increased irregularity in the balance between sympathetic and parasympathetic nervous system activity, may indicate a worsening heart failure condition of patient 4.

Thus, in some examples, the processing circuitry may determine an HBV difference threshold value or HBV threshold value based on fluctuations in a difference between first and second values of at least one HBV metric, or fluctuations in current values of at least one HBV metric, occurring across one or more previous activity cycles of patient 4. In examples in which the processing circuitry determines the heart failure status of patient 4 based on a comparison of a difference between first and second values of at least one HBV metric to an HBV difference threshold, the HBV difference threshold value may be based on one or more values of the difference between the first and second values of the at least one HBV metric that correspond to one or more previous activity cycles of patient 4. In examples in which the processing circuitry determines the heart failure status of patient 4 based on a comparison of a difference between current and baseline values of at least one HBV metric to at least one corresponding HBV threshold, the predetermined period of time may be a current predetermined period of time, and at least one corresponding HBV threshold value may be based on one or more corresponding previous values of the at least one HBV metric of patient 4 that correspond to one or more previous predetermined periods of time.

In any such examples, if the one or more previous activity cycles of patient 4 indicate increasingly irregular cardiac function, the processing circuitry may modify a threshold value to provide greater sensitivity to continued fluctuation, such as by raising a threshold value associated with a lower end of an HBV difference range or lowering a threshold value associated with a higher end of an HBV difference range. In this manner, the processing circuitry may modify the sensitivity of a technique for determining heart failure status by accounting for trends in in determined values of one or more HBV metrics of patient 4, which may further help enable detection of changes in a heart failure status of patient 4.

Thus, as described above, the operating parameters of IMD 10 readily may be customized to meet the needs of patient 4, such as by setting baseline and/or threshold values based on the individual attributes of patient 4, such as a heart failure condition or other medical condition of patient and/or an existing medication regimen of patient 4. The extent and ease of customizability of IMD 10 may provide numerous benefits. For example, customizability of IMD 10 to reflect a heart failure condition or existing medication regimen of patient 4 helps ensure that appropriate therapies are prescribed for patient 4, thereby reducing a possibility of human error in prescribing treatment. In addition, in examples in which the processing circuitry (e.g., of IMD 10) one or more baseline and/or threshold values for patient 4, burdens on the clinician's time may be reduced, which may reduce the time needed for an office visit and promote efficient treatment. Moreover, as discussed above, techniques for using medical device system 2 to determine a heart failure status of patient 4 between clinician visits may help avoid adverse medical events, which may lead to better clinical outcomes such as improved quality of life for patient 4 or reduced medical expenses.

External device 12 may be a computing device (e.g., used in a home, ambulatory, clinic, or hospital setting) to communicate with IMD 10 via wireless telemetry. External device 12 may include or be coupled to a remote patient monitoring system, such as Carelink®, available from Medtronic plc, of Dublin, Ireland. External device 12 may be, as an example, a programmer, external monitor, or a consumer device (e.g., a smart phone). In some examples, external device 12 may receive data, alerts, patient physiological information, or other information from IMD 10.

External device 12 may be used to program commands or operating parameters into IMD 10 for controlling its functioning (e.g., when configured as a programmer for IMD 10). In some examples, external device 12 may be used to interrogate IMD 10 to retrieve data, including device operational data as well as physiological data accumulated in IMD memory. Such interrogation may occur automatically according to a schedule and/or may occur in response to a remote or local user command. Programmers, external monitors, and consumer devices are examples of external devices 12 that may be used to interrogate IMD 10. Examples of communication techniques used by IMD 10 and external device 12 include radiofrequency (RF) telemetry, which may be an RF link established via Bluetooth, WiFi, or medical implant communication service (MICS). In some examples, external device 12 may include a user interface configured to allow patient 4, a clinician, or another user to remotely interact with IMD 10. In some such examples, external device 12, and/or any other device of medical device system 2, may be a wearable device, (e.g., in the form of a watch, necklace, or other wearable item). Such wearable devices may include one or more electrodes or other sensors configured for sensing signals used in determining values of at least one HBV metric in accordance with the techniques described herein.

Medical device system 2 is an example of a medical device system configured to monitor a heart failure status of patient 4 and facilitate updates to patient 4's treatment (e.g., for a heart failure condition) as needed between clinician visits. The techniques described herein may be performed by processing circuitry of a device of medical device system 2, such as processing circuitry of IMD 10. Additionally, or alternatively, the techniques described herein may be performed, in whole or in part, by processing circuitry of external device 12, and/or by processing circuitry of one or more other implanted or external devices or servers (not shown). Examples of the one or more other implanted or external devices may include an implanted, multi-channel cardiac pacemaker, ICD, IPG, leadless (e.g., intracardiac) pacemaker, extravascular pacemaker and/or ICD, or other IMD or combination of such IMDs configured to deliver CRT to heart 6, an external monitor, or a drug pump.

Communication circuitry of each of the devices of medical device system 2 (e.g., IMD 10 and external device 12) may enable the devices to communicate with one another. In addition, although one or more sensors (e.g., electrodes) are described herein as being positioned on a housing of IMD 10, in other examples, such sensors may be positioned on a housing of another device implanted in or external to patient 4. In such examples, one or more of the other devices may include processing circuitry configured to receive signals from the electrodes or other sensors on the respective devices and/or communication circuitry configured to transmit the signals from the electrodes or other sensors to another device (e.g., external device 12) or server.

Figure 2:
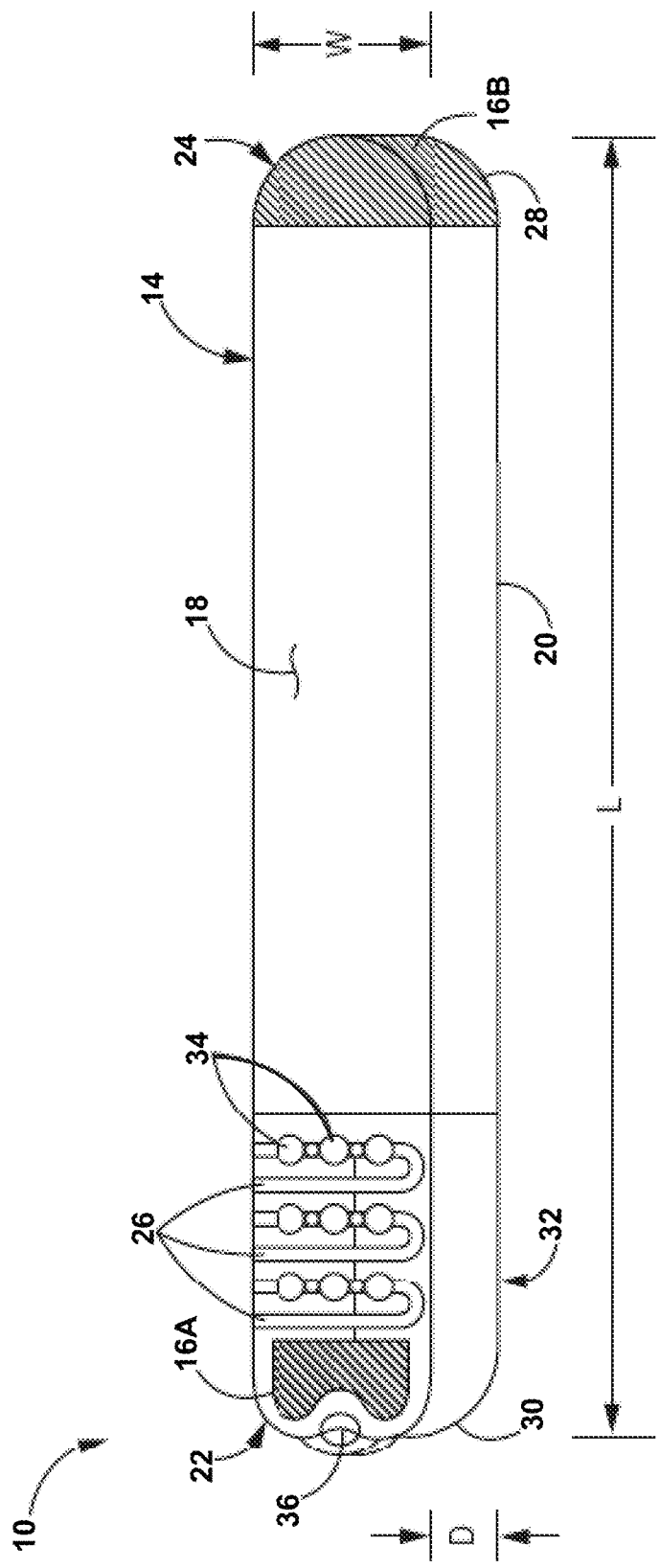
FIG. 2 is a conceptual drawing illustrating an example configuration of the leadless implantable medical device of the medical device system of FIG. 1.
Figure 3:
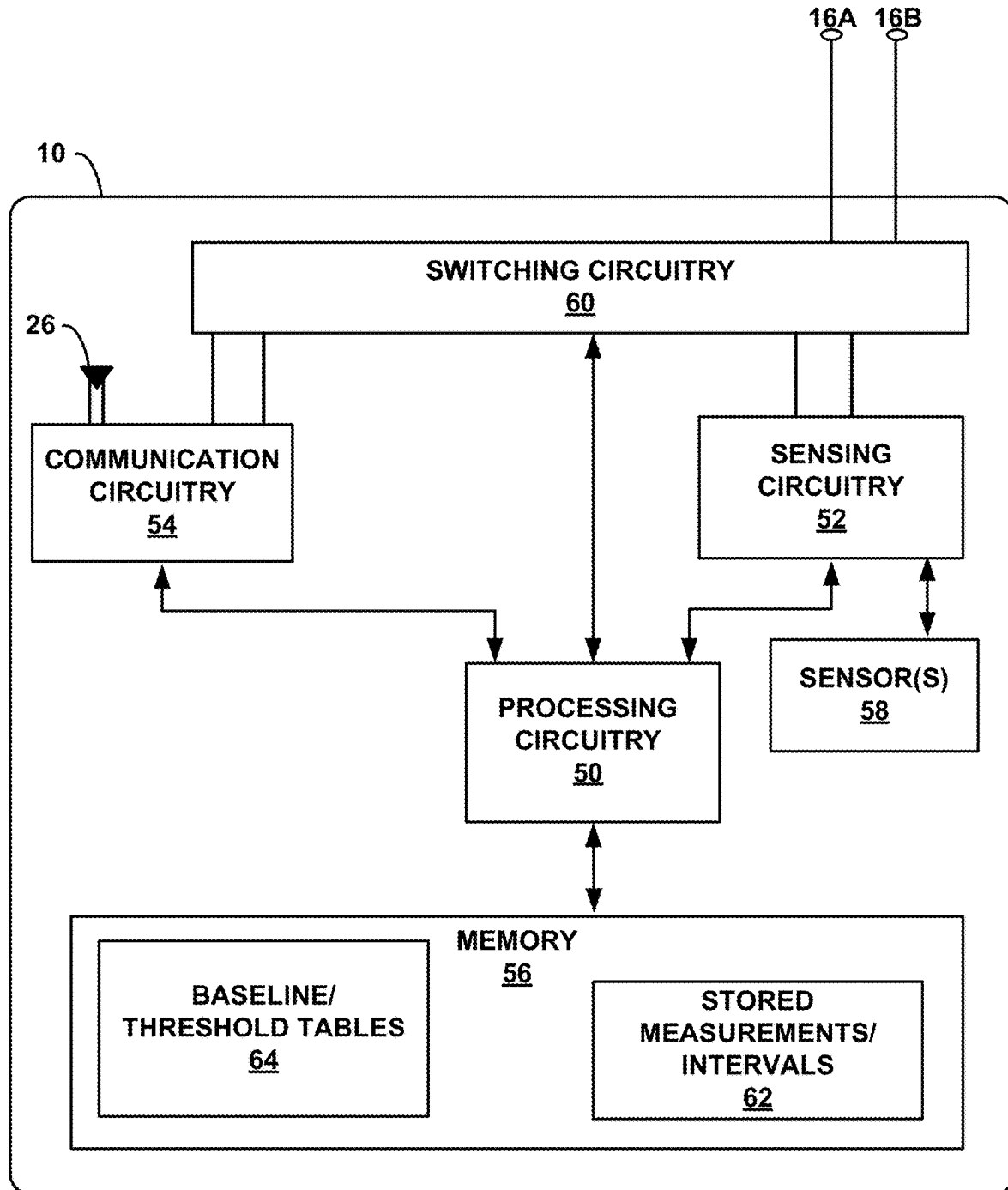
FIG. 3 is a functional block diagram illustrating another perspective of the example configuration of the leadless implantable medical device of FIG. 1.
Figure 4A:
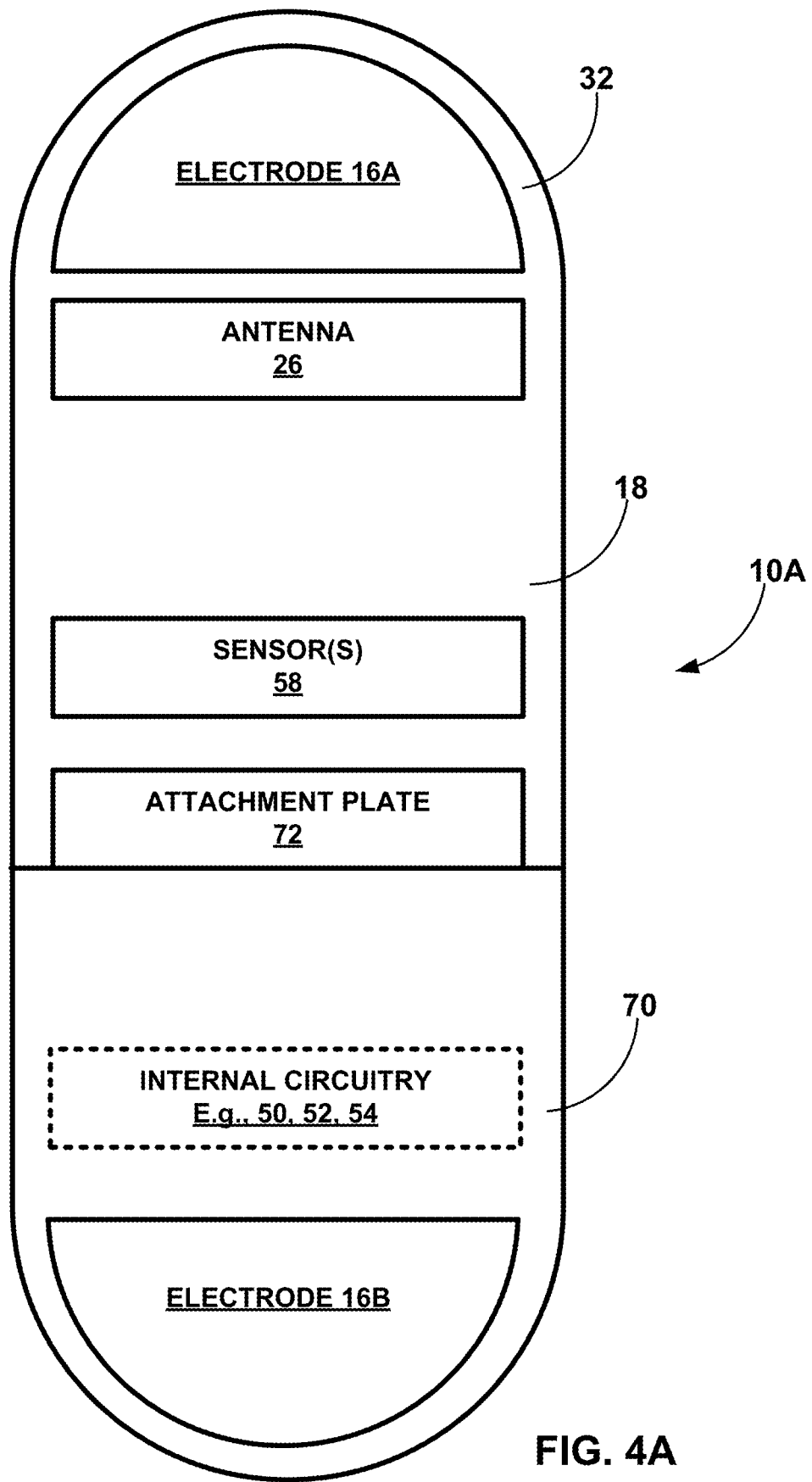
FIGS. 4A and 4B are block diagrams illustrating other example leadless implantable medical devices substantially similar to the implantable medical device of FIG. 1.
Figure 4B:
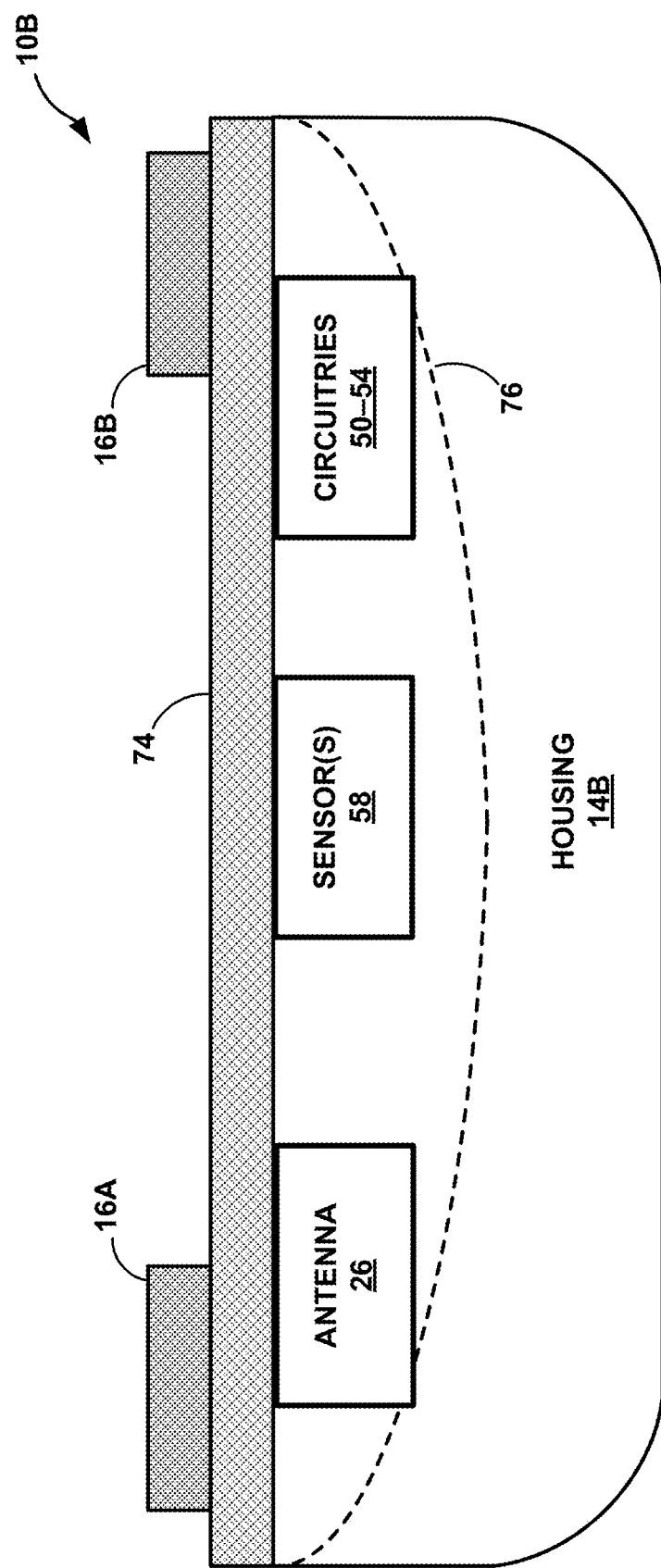

FIGS. 2-4B illustrate various aspects and example arrangements of IMD 10 of FIG. 1. For example, FIG. 2 conceptually illustrates an example physical configuration of IMD 10. FIG. 3 is a block diagram illustrating an example functional configuration of IMD 10. FIGS. 4A and 4B illustrate additional views of an example physical and functional configuration of IMD 10. It should be understood that any of the examples of IMD 10 described below with respect to FIGS. 2-4B may be used to implement the techniques described herein for determining a heart failure status of patient 4.

FIG. 2 is a conceptual drawing illustrating an example configuration of IMD 10 of FIG. 1. In the example shown in FIG. 2, IMD 10 may comprise a leadless, subcutaneously-implantable monitoring device having a housing 14, a proximal electrode 16A, and a distal electrode 16B. Housing 14 encloses electronic circuitry located inside the IMD 10, and protects the circuitry contained therein from fluids such as body fluids. In some examples, 14 may comprise first major surface 18, second major surface 20, proximal end 22, and distal end 24. Proximal electrode 16A and distal electrode 16B may be positioned near respective proximal and distal ends 22 and 24 of IMD 10, such that a spacing between proximal electrode 16A and distal electrode 16B may range from about 30-55 mm, about 35-55 mm, or about 40-55 mm, or more generally from about 25-60 mm. In some examples, IMD 10 may include one or more additional electrodes and/or one or more other sensors (not shown), which may be positioned on one or both of major surfaces 18, 20 of IMD 10. In any such examples, electrical feedthroughs may provide electrical connection of electrodes 16A, 16B or other sensors to circuitry within housing 14.

In the example shown in FIG. 2, IMD 10 is defined by a length L, a width W, and thickness or depth D. In this example, IMD 10 is in the form of an elongated rectangular prism in which length L is significantly greater than width W, and in which width W is greater than depth D. However, other configurations of IMD 10 are contemplated, such as those in which the relative proportions of length L, width W, and depth D vary from those described and shown in FIG. 2. In some examples, the geometry of the IMD 10, such as the width W being greater than the depth D, may be selected to allow IMD 10 to be inserted under the skin of the patient using a minimally invasive procedure and to remain in the desired orientation during insertion. In addition, IMD 10 may include radial asymmetries (e.g., the rectangular shape) along a longitudinal axis of IMD 10, which may help maintain the device in a desired orientation following implantation.

Overall, IMD 10 may have a length L of about 20-30 mm, about 40-60 mm, or about 45-60 mm. In some examples, the width W of first major surface 18 may range from about 3-10 mm, and may be any single width or range of widths between about 3-10 mm. In some examples, a depth D of IMD 10 may range from about 2-9 mm. In other examples, the depth D of IMD 10 may range from about 2-5 mm, and may be any single or range of depths from about 2-9 mm. In any such examples, IMD 10 is sufficiently compact to be implanted within the subcutaneous space of patient 4 in the region of a pectoral muscle.

IMD 10 may have a geometry and size designed for ease of implantation and patient comfort. For example, IMD 10 may have a volume of 3 cubic centimeters ($cm^3$) or less, 1.5 $cm^3$ or less, or any volume therebetween. As illustrated in FIG. 2, proximal end 22 and distal end 24 may be rounded, which may reduce discomfort and/or irritation to surrounding tissue when IMD 10 implanted under the skin of patient 4. An example configuration of IMD 10, including an instrument and method for inserting IMD 10 is described in U.S. Patent Publication No. 2014/0276928, incorporated herein by reference in its entirety. An example configuration of IMD 10 also is described in U.S. Patent Publication No. 2016/0310031, incorporated herein by reference in its entirety.

In some examples, IMD 10 may be configured for implantation within patient 4 such that first major surface 18 of IMD 10 faces outward towards the skin when IMD 10 is inserted within patient 4 and second major surface 20 is faces inward toward musculature of patient 4. First and second major surfaces 18, 20 may face in directions along a sagittal axis of patient 4, as illustrated in FIG. 1, and this orientation may be maintained upon implantation due to the dimensions of IMD 10. Additionally, or alternatively, IMD 10 may be configured for implantation within patient 4 in one or more other orientations relative to one or more anatomical landmarks of patient 4.

In the example shown in FIG. 2, proximal end 22 of IMD 10 includes header assembly 32 having one or more of integrated antenna 26, anti-migration projections 34, and suture hole 36. Integrated antenna 26 is located on the same major surface (e.g., first major surface 18) as electrode 16A, and may be an integral part of header assembly 32. In other examples, integrated antenna 26 may be formed on the major surface opposite from electrode 16A or may be incorporated within housing 14 of IMD 10. Antenna 26 may be configured to transmit or receive electromagnetic signals for communication. For example, antenna 26 may be configured to transmit to or receive signals from a programmer via inductive coupling, electromagnetic coupling, tissue conductance, Near Field Communication (NFC), Radio Frequency Identification (RFID), Bluetooth, WiFi, or other proprietary or non-proprietary wireless telemetry communication schemes. Antenna 26 may be coupled to communication circuitry of IMD 10, which may drive antenna 26 to transmit signals to external device 12. Antenna 26 may transmit signals received from external device 12 to processing circuitry of IMD 10 via the communication circuitry.

IMD 10 may include several features for retaining IMD 10 in position once subcutaneously implanted in patient 4. For example, as shown in FIG. 2, housing 14 may include anti-migration projections 34 positioned adjacent integrated antenna 26. Anti-migration projections 34 may comprise a plurality of bumps or protrusions extending away from first major surface 18 and may reduce or prevent movement of IMD 10 after implantation in patient 4. In other examples, anti-migration projections 34 may be located on the opposite major surface as proximal electrode 16A and/or integrated antenna 26. In addition to or instead of anti-migration projections 34, a portion of housing 14 (e.g., header assembly 32) may define a suture hole 36, which may enable a clinician to suture IMD 10 to patient tissue to reduce or prevent movement of IMD 10 after implantation in patient 4. In the example of FIG. 2, suture hole 36 is defined by a portion of header assembly 32 adjacent to proximal electrode 16A. In some examples, header assembly 32 may comprise a molded header assembly made from a polymeric material, which may be integral with or separable from the main portion of IMD 10.

In examples in which the processing circuitry of medical device system 2 is configured to determine values of at least one HBV metric based on a cardiac electrogram signal, IMD 10 may include a plurality of electrodes. For example, as illustrated in FIG. 2, IMD 10 may include a proximal electrode 16A and a distal electrode 16B. As shown in the illustrated example, proximal electrode 16A may be positioned on header assembly 32, and distal electrode 16B may be formed from an uninsulated distal portion of conductive housing 14. Proximal electrode 16A and distal electrode 16B may be positioned near respective proximal and distal ends 22 and 24 of IMD 10, such that a spacing between proximal electrode 16A and distal electrode 16B may range from about 30-55 mm, about 35-55 mm, or about 40-55 mm, or more generally from about 25-60 mm. In some examples, IMD 10 also may include one or more additional electrodes (not shown) positioned on one or both of major surfaces 18, 20 of IMD 10. In any such examples, electrical feedthroughs may provide electrical connection of electrodes 16A, 16B, any additional electrodes, and antenna 26, to circuitry within housing 14.

In the example shown in FIG. 2, proximal electrode 16A is in close proximity to proximal end 22, and distal electrode 16B is in close proximity to distal end 24 of IMD 10. In this example, distal electrode 16B is not limited to a flattened, outward facing surface, but may extend from first major surface 18, around rounded edges 28 or end surface 30, and onto the second major surface 20 in a three-dimensional curved configuration. As illustrated, proximal electrode 16A is located on first major surface 18 and is substantially flat and outward facing. However, in other examples not shown here, proximal electrode 16A and distal electrode 16B both may be configured like proximal electrode 16A shown in FIG. 2, or both may be configured like distal electrode 16B shown in FIG. 2. Any of electrodes 16A, 16B may be formed of a biocompatible conductive material. For example, any of electrodes 16A, 16B may be formed from any of stainless steel, titanium, platinum, iridium, or alloys thereof. In addition, electrodes of IMD 10 may be coated with a material such as titanium nitride or fractal titanium nitride, although other suitable materials and coatings for such electrodes may be used.

Proximal electrode 16 and distal electrode 16B may be used to sense cardiac electrogram signals when IMD 10 is implanted subcutaneously in patient 4. In the techniques described herein, processing circuitry of IMD 10 may determine values of at least one HBV metric based on cardiac electrogram signals. In some examples, the processing circuitry also may determine whether cardiac electrogram signals of patient 4 are indicative of arrhythmia (e.g., the presence or absence of atrial fibrillation and a ventricular rate during atrial fibrillation) or other abnormalities, which the processing circuitry may evaluate in determining whether a cardiac function of patient 4 has changed.

For example, the processing circuitry may determine that the cardiac function of patient 4 has changed based on determining the presence of atrial fibrillation. Thus, the presence of atrial fibrillation, alone or in combination with values of at least one HBV metric, may warrant an updated diagnosis of a heart failure condition of patient 4. In such examples, instructions for a medical intervention that an external device (e.g., external device 12) may transmit to a user device may be based, at least in part, on the determination of atrial fibrillation. Additionally, or alternatively, the processing circuitry may treat the presence of atrial fibrillation as noise in the cardiac electrogram signal when determining the values of the at least one HBV metric. In some such examples, the processing circuitry may discard HBV values determined during an episode of atrial fibrillation, or apply filtering or other data or signal processing techniques to mitigate the influence of the atrial fibrillation on the determined HBV values. In any such examples, the cardiac electrogram signals may be stored in a memory of the IMD 10, and data derived from the cardiac electrogram signals may be transmitted via integrated antenna 26 to another medical device, such as external device 12.

In some examples, IMD 10 may include one or more additional sensors, such as one or more accelerometers, microphones, and/or pressure sensors (not shown). Such accelerometers may be 3D accelerometers configured to generate signals indicative of one or more types of movement of the patient, such as gross body movement (e.g., activity) of the patient, patient posture, movements and/or sounds associated with the beating of heart 6, respiration rate, or others. Such microphones may be configured to generate signals indicative of sounds associated with the beating of heart 6 and/or respiration of patient 4 sounds, and/or dyspnea, on the basis of which the processing circuitry may determine a heart rate, a respiration rate or depth of patient 4, or other parameter associated with such sounds. Such pressure sensors may be configured to generate signals indicative of changes in pressure associated with the beating of heart 6, on the basis of which the processing circuitry may determine a heart rate of patient 4.

In some examples, the processing circuitry may determine one or more aspects of an activity state of patient 4, such as whether the activity state of patient 4 satisfies at least one inactivity criterion, based on at least one signal received from the one or more accelerometers and/or pressure sensors. Additionally, or alternatively, the processing circuitry may determine one or more aspects of the activity state of patient 4 based on one or more signals received from electrodes of medical device system 2 (e.g., electrodes 16A, 16B) that may be indicative of a heart rate and/or a respiration parameter of patient 4. For example, the processing circuitry may determine whether at least one of an activity level, posture, heart rate, body temperature, sounds associated with dyspnea, pulmonary artery pressure, sleep/non-sleep brain waves, or a respiration rate or depth of patient 4, and/or a time of day, is indicative of patient 4 being substantially inactive (e.g., asleep) or active (e.g., awake) based on the one or more signals received from the one or more accelerometers, microphones, pressure sensors, other types of sensors, electrodes 16A, 16B, and/or other electrodes that may be included in IMD 10 or in another device of medical device system 2.

In examples in which at least one inactivity criterion comprises a posture of patient 4, the processing circuitry may be configured to determine that an activity state of patient 4 satisfies the at least one inactivity criterion by determining that patient 4 is lying down and/or asleep based on the at least one signal received from the one or more accelerometers. Additionally, or alternatively, the processing circuitry may determine that patient 4 is asleep based on a heart rate of patient 4, such as based on a determination that a heart rate of patient 4 is at or below a threshold value associated with a sleep state for a predetermined period of time. Thus, in some example techniques for determining the heart failure status of patient 4, the processing circuitry may determine a first value of at least one HBV metric while the activity state of patient 4 satisfies the at least one inactivity criterion by determining the first value of the at least one HBV metric while patient 4 is lying down and/or asleep.

In some such examples, the processing circuitry may determine that the activity state of patient 4 no longer satisfies the at least one inactivity criterion by determining that patient 4 is in an upright posture and/or awake based on the at least one first signal. Additionally, or alternatively, the processing circuitry may determine that patient 4 is awake based on a heart rate of patient 4, such as based on a determination that a heart rate of patient 4 is at or above a threshold value associated with a waking state for a predetermined period of time. Thus, in some example techniques for determining the heart failure status of patient 4, the processing circuitry may determine a second value or current value of at least one HBV metric while the activity state of patient 4 no longer satisfies the at least one inactivity criterion by determining the second value or current value of the at least one HBV metric while patient 4 is in the upright posture and/or awake, within a predetermined period of time (e.g., within about 30 minutes) after determining patient 4 is in the upright posture and/or has awakened from a sleep state.

In some examples, the processing circuitry may determine values of one or more HBV metrics based on signals indicative of heart rate from the one or more accelerometers, microphones, and/or pressure sensors, in addition to or instead determining values of the one or more HBV metrics of based on a cardiac electrogram signal received from electrodes 16A, 16B. In any such examples, the processing circuitry may determine a value of an HBV metric based on a plurality of values. For example, in example techniques in which the processing circuitry determines a heart failure status of patient 4 based on a difference between first and second values of at least one HBV metric, the processing circuitry may determine one or both of the first value and the second value of the at least one HBV metric by determining a corresponding representative first and/or second value of the at least one HBV metric based on a corresponding plurality of first and/or second values of the at least one HBV metric. Similarly, in example techniques in which the processing circuitry determines a heart failure status of patient 4 based on a difference between a current value of at least one HBV metric and a baseline value of the at least one HBV metric, the processing circuitry may determine one or both of the current value and the baseline value of the at least one HBV metric by determining a corresponding representative current value of the at least one HBV metric based on a corresponding plurality of current and/or baseline values of the at least one HBV metric.

In any such examples, the processing circuitry may determine each of a plurality of values of an HBV metric by intermittently sampling values of the HBV metric during a period of time. For example, the processing circuitry may determine values of the HBV metric at 3-minute intervals for a 30 second period each over ten measurement cycles for a total duration of 30 minutes, although any other suitable intervals, number of cycles, or time periods may be used. The processing circuitry then may determine a representative value of the HBV metric based on the values of the HBV metric collected during the period of time. In some examples, the processing circuitry may reject any outlier values of the HBV metric, which may help enhance the accuracy of the determination of the heart failure status of patient 4. The processing circuitry may average the collected measurements, less any rejected outlier values, to determine the representative value, although any other suitable method of data analysis may be used.

Although processing circuitry of IMD 10 is described above as being configured to receive signals from the one or more accelerometers, one or more microphones, one or more pressure sensors and/or electrodes 16A, 16B and determine a value of one or more parameters of patient 4 based on such signals, any steps described herein as being carried out by processing circuitry of IMD 10 may carried out by processing circuitry of one or more devices. For example, processing circuitry of external device 12, or any other suitable implantable or external device or server, may be configured to receive signals from the one or more accelerometers, one or more microphones, one or more pressure sensors and/or electrodes 16A, 16B, such as via communication circuitry of IMD 10.

FIG. 3 is a functional block diagram illustrating an example configuration of IMD 10 of FIGS. 1 and 2. As shown in FIG. 3, IMD 10 includes processing circuitry 50 sensing circuitry 52, communication circuitry 54, memory 56, sensors 58, and switching circuitry 60, in addition to previously-described electrodes 16A, 16B, one or more of which may be disposed within housing 14 of IMD 10. In some examples, memory 56 includes computer-readable instructions that, when executed by processing circuitry 50, cause IMD 10 and processing circuitry 50 to perform various functions attributed to IMD 10 and processing circuitry 50 herein. Memory 56 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

In some examples, timing and/or control aspects of processing circuitry 50 may comprise a dedicated hardware circuit, such as an ASIC, separate from other aspects of processing circuitry 50, such as a microprocessor, or a software module executed by a component of processing circuitry 50 (e.g., a microprocessor or ASIC). Timing and/or control aspects of processing circuitry 50 may monitor the passage of time to determine when a period of time has elapsed. For example, the timing and/or control aspects of processing circuitry 50 may determine, prior to processing circuitry 50 determining that the activity state of patient 4 no longer satisfies at least one inactivity criterion, that a period of time during which the activity state of the patient is expected to satisfy the at least one inactivity criterion (e.g., a period of time during which patient 4 is expected to be asleep) has elapsed and that a period of time during which the activity state of patient 4 is expected to no longer satisfy the at least one inactivity criterion (e.g., a period of time during which patient 4 is expected to awaken) has begun. The period of time during which the activity state of patient 4 is expected to no longer satisfy the at least one inactivity criterion may include at least a portion of the predetermined period of time after an activity state of patient 4 has increased during which processing circuitry 50 may determine a second value or a current value of at least one HBV metric. In some such examples in which IMD 10 includes one or more accelerometers, processing circuitry 50 may cross-reference an indication by timing and control circuitry that a period of time has elapsed or begun with accelerometer data, such as to confirm whether patient 4 is asleep or awake as expected.

In some examples, processing circuitry 50 may determine the activity state of patient 4 and/or values of at least one HBV metric more frequently when the activity state of patient 4 is expected to no longer satisfy the at least one inactivity criterion than when patient 4 is expected to satisfy the at least one inactivity criterion, which may enable processing circuitry 50 to identify or approximate the time at which the activity state of patient 4 ceases to satisfy the at least one inactivity criterion while conserving power during times when such close monitoring is not needed. In some examples, timing and/or control aspects of processing circuitry 50 may control IMD 10 to transmit a heart failure status of patient 4 to external device 12, such as at the conclusion of a monitoring interval.

Memory 56 may store determined values of one or more HBV metrics of patient 4 and/or one or more intervals or time periods according to which processing circuitry 50 may determine values of one or more HBV metrics in stored measurements/intervals 62. Memory 56 also may store baseline and/or threshold values, which processing circuitry 50 may determine during a learning phase of IMD 10, in tables 64. In some examples, processing circuitry may determine an HBV difference threshold value based on a determined baseline difference between a baseline first value of the at least one HBV metric and a baseline second value of the at least one HBV metric.

For example, processing circuitry 50 may receive at least one baseline second signal from at least electrodes of IMD 10 (e.g., electrodes 16A, 16B). Processing circuitry 50 then may determine a baseline first value of the at least one HBV metric and a baseline second value of the at least one HBV metric based on the at least one baseline second signal. As with other first and second values of the at least one HBV metric, processing circuitry may determine the baseline first value of the at least one HBV metric while an activity state of patient 4 satisfies at least one inactivity criteria and determine the second baseline value of the at least one HBV value within a predetermined period of time of determining that the activity state of patient 4 no longer satisfies the at least one inactivity criteria. Processing circuitry 50 then may determine a baseline difference between the baseline first value of the at least one HBV metric and the baseline second value of the at least one HBV metric and determine the HBV difference threshold value based on the baseline difference between the baseline first and second values of the at least one HBV metric.

Processing circuitry 50 similarly may determine one or more of baseline and/or threshold values in examples in which processing circuitry 50 determines the heart failure status of patient 4 based on a difference between a current value of at least one HBV metric and a baseline value of the at least one HBV metric. For example, processing circuitry 50 may determine a patient-specific baseline value of the at least one HBV metric by receiving at least one baseline second signal from sensors 58 (e.g., from at least two electrodes of IMD 10) and determine the patient-specific value of the at least one baseline HBV metric based on the baseline at least one second signal. In any such examples, tables 64 may include pre-programmed baseline and/or threshold values that a clinician may select for patient 4 during setup of IMD 10 or manually enter based on the clinician's assessments of patient 4.

Sensing circuitry 52 and communication circuitry 54 may be selectively coupled to electrodes 16A, 16B via switching circuitry 60 as controlled by processing circuitry 50. Sensing circuitry 52 may monitor signals from electrodes 16A, 16B in order to monitor electrical activity of heart and produce a cardiac electrogram from which processing circuitry 50 may determine values of a heart rate of patient 4 and/or values of one or more HBV metrics of patient 4. In some examples in which IMD 10 includes one or more accelerometers, microphones, and/or pressure sensors, sensing circuitry 52 also may monitor signals from sensors 58, which may include such accelerometers, microphones, and/or pressure sensors. In some examples, sensing circuitry 52 may include one or more filters and amplifiers for filtering and amplifying signals received from one or more of electrodes 16A, 16B and/or other sensors 58.

In some examples, sensing circuitry 52 and/or processing circuitry 50 may include a rectifier, filter and/or amplifier, a sense amplifier, comparator, and/or analog-to-digital converter. Upon receiving signals from electrodes 16A, 16B and/or other sensors 58 via sensing circuitry 52, processing circuitry 50 may determine values of at least one HBV metric of patient 4. Processing circuitry 50 then may determine a heart failure status of patient 4 based on a difference between first and second values of at least one HBV metric or a difference between current and baseline values of at least one HBV metric, such as based on whether such a difference satisfies a corresponding HBV difference threshold value or HBV threshold value stored in tables 64.

Communication circuitry 54 may include any suitable hardware, firmware, software or any combination thereof for communicating with another device, such as external device 12 or another medical device or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. In some examples, communication circuitry 54 may communicate with external device 12. In addition, processing circuitry 50 may communicate with a networked computing device via an external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device. In some examples, the clinician may select one or more baseline and/or threshold values associated with one or more HBV metrics, times of day during which patient 4 is expected to be awake or asleep, predetermined periods of time, a number of measurements to be completed during a period, or other parameters of IMD 10.

One or more components of IMD 10 may be coupled a power source, which may include a rechargeable or non-rechargeable battery positioned within housing 14 of IMD 10. A non-rechargeable battery may be selected to last for several years, while a rechargeable battery may be inductively charged from an external device, e.g., on a daily or weekly basis.

FIGS. 4A and 4B illustrate two additional example IMDs that may be substantially similar to IMD 10 of FIGS. 1-3, but which may include one or more additional features. The components of FIGS. 4A and 4B may not necessarily be drawn to scale, but instead may be enlarged to show detail. FIG. 4A is a block diagram of a top view of an example configuration of an IMD 10A. FIG. 4B is a block diagram of a side view of example IMD 10B, which may include an insulative layer as described below.

FIG. 4A is a conceptual drawing illustrating another example IMD 10A that may be substantially similar to IMD 10 of FIG. 1. In addition to the components illustrated in FIGS. 1-3, the example of IMD 10 illustrated in FIG. 4A also may include a body portion 70 and an attachment plate 72. Attachment plate 72 may be configured to mechanically couple header 32 to body portion 70 of IMD 10A. Body portion 70 of IMD 10A may be configured to house one or more of the internal components of IMD 10 illustrated in FIG. 3, such as one or more of processing circuitry 50, sensing circuitry 52, communication circuitry 54, memory 56, and/or internal components of sensors 58. In some examples, body portion 70 may be formed of one or more of titanium, ceramic, or any other suitable biocompatible materials.

FIG. 4B is a conceptual drawing illustrating another example IMD 10B that may include components substantially similar to IMD 10 of FIG. 1. In addition to the components illustrated in FIGS. 1-3, the example of IMD 10B illustrated in FIG. 4B also may include a wafer-scale insulative cover 74, which may help insulate electrical signals passing between electrodes 16A, 16B on housing 14B and processing circuitry 50. In some examples, insulative cover 74 may be positioned over an open housing 14 to form the housing for the components of IMD 10B. One or more components of IMD 10B (e.g., antenna 26, processing circuitry 50, sensing circuitry 52, and/or communication circuitry 54 may be formed on a bottom side of insulative cover 74, such as by using flip-chip technology. Insulative cover 74 may be flipped onto a housing 14B. When flipped and placed onto housing 14B, the components of IMD 10B formed on the bottom side of insulative cover 74 may be positioned in a gap 78 defined by housing 14B. Housing 14B may be formed from titanium or any other suitable material (e.g., a biocompatible material), and may have a thickness of about 200 micrometers to about 500 micrometers. These materials and dimensions are examples only, and other materials and other thicknesses are possible for devices of this disclosure.

Figure 5:
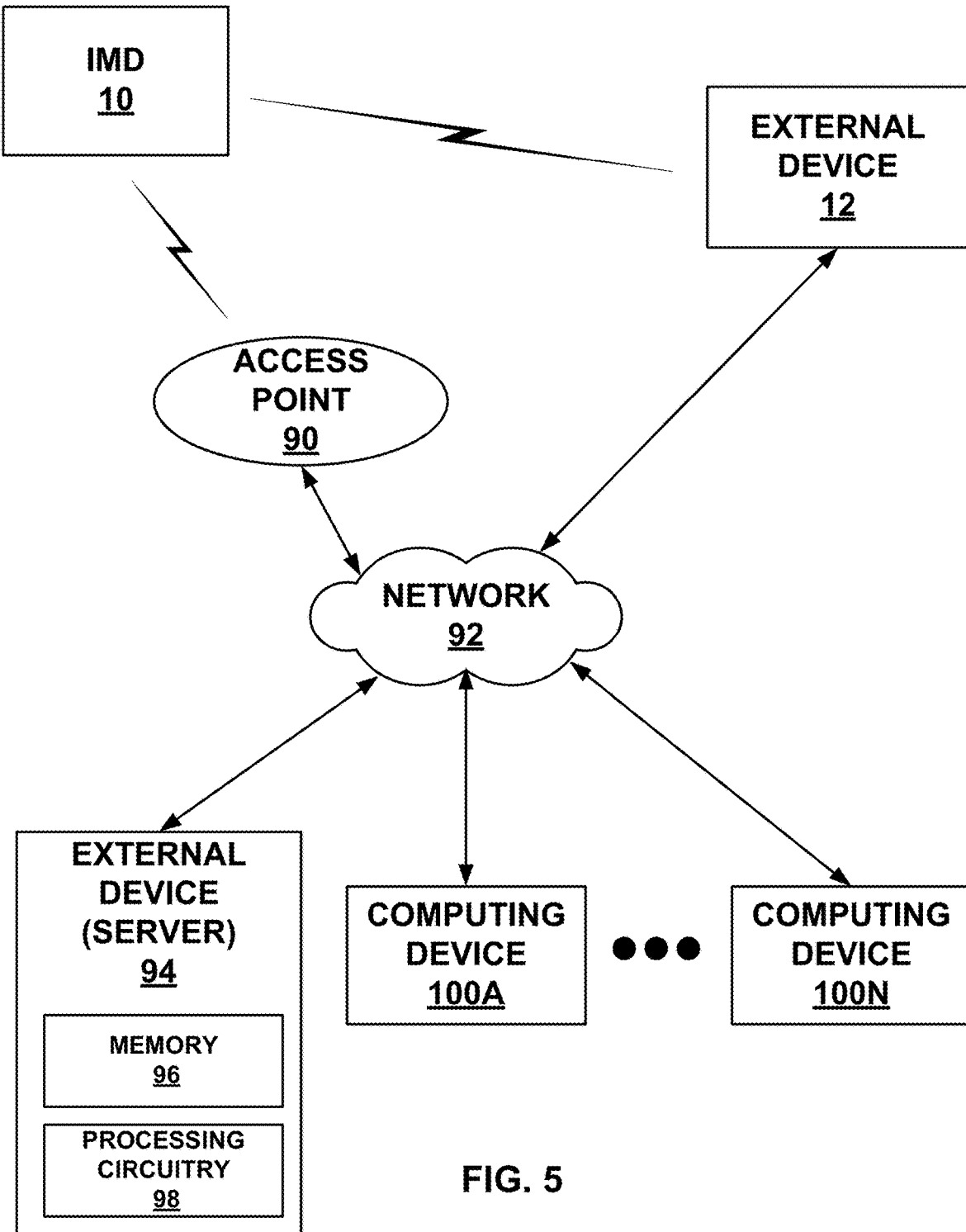
FIG. 5 is a block diagram illustrating an example system that includes an external device, such as a server, and one or more computing devices that are coupled to the leadless implantable medical device of FIG. 1 and the external device of FIG. 1 via a network.

FIG. 5 is a functional block diagram illustrating an example system that includes an access point 90, a network 92, external computing devices, such as a server 94, and one or more other computing devices 100A-100N, which may be coupled to IMD 10, external device 12, and external device 12 via network 92. In this example, IMD 10 may use communication circuitry 54 to communicate with external device 12 via a first wireless connection, and to communicate with an access point 90 via a second wireless connection. In the example of FIG. 5, access point 90, external device 12, server 94, and computing devices 100A-100N are interconnected and may communicate with each other through network 92.

Access point 90 may comprise a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet, smartphone, or wearable device (e.g., in the form of a watch, necklace, or other wearable item), that may be co-located with the patient. Such wearable devices may include one or more electrodes or other sensors configured for sensing signals used in determining values of at least one HBV metric in accordance with the techniques described herein. As discussed above, IMD 10 may be configured to transmit data, such as current values and heart failure statuses, to external device 12. In addition, access point 90 may interrogate IMD 10, such as periodically or in response to a command from the patient or network 92, in order to retrieve current values or heart failure statuses determined by processing circuitry 50 of IMD 10, or other operational or patient data from IMD 10. Access point 90 may then communicate the retrieved data to server 94 via network 92.

In some cases, server 94 may be configured to provide a secure storage site for data that has been collected from IMD 10, and/or external device 12. In some cases, server 94 may assemble data in web pages or other documents for viewing by trained professionals, such as clinicians, via computing devices 100A-100N. One or more aspects of the illustrated system of FIG. 5 may be implemented with general network technology and functionality, which may be similar to that provided by the Medtronic CareLink® Network developed by Medtronic plc, of Dublin, Ireland.

In some examples, one or more of computing devices 100A-100N (e.g., device 100A) may be a tablet or other smart device located with a clinician, by which the clinician may program, receive alerts from, and/or interrogate IMD 10. For example, the clinician may access determined values of one or more HBV metrics of patient 4 and/or other information associated with the heart failure status of patient 4 through device 100A, such as when patient 4 is in in between clinician visits, to check on a heart failure status of patient 4 as desired. In some examples, the clinician may enter instructions for a medical intervention for patient 4 into an app in device 100A, such as based on a heart failure status of patient 4 determined by IMD 10 and/or other patient data known to the clinician. Device 100A then may transmit the instructions for medical intervention to another of computing devices 100A-100N (e.g., device 100B) located with patient 4 or a caregiver of patient 4. For example, such instructions for medical intervention may include an instruction to change a drug dosage, timing, or selection, to schedule a visit with the clinician, or to seek medical attention. In further examples, device 100B may generate an alert to patient 4 based on a health status of patient 4 determined by IMD 10, which may enable patient 4 proactively to seek medical attention prior to receiving instructions for a medical intervention. In some examples, the alert generated by device 100B may include an updated diagnosis of one or more health conditions such as a heart failure condition. For example, the alert may include a diagnosis that a heart failure condition of patient 4 has progressed from a first type of heart failure condition to a second type of heart failure condition. In this manner, patient 4 may be empowered to take action, as needed, to address his or her heart failure status, which may help improve clinical outcomes for patient 4.

Figure 6:
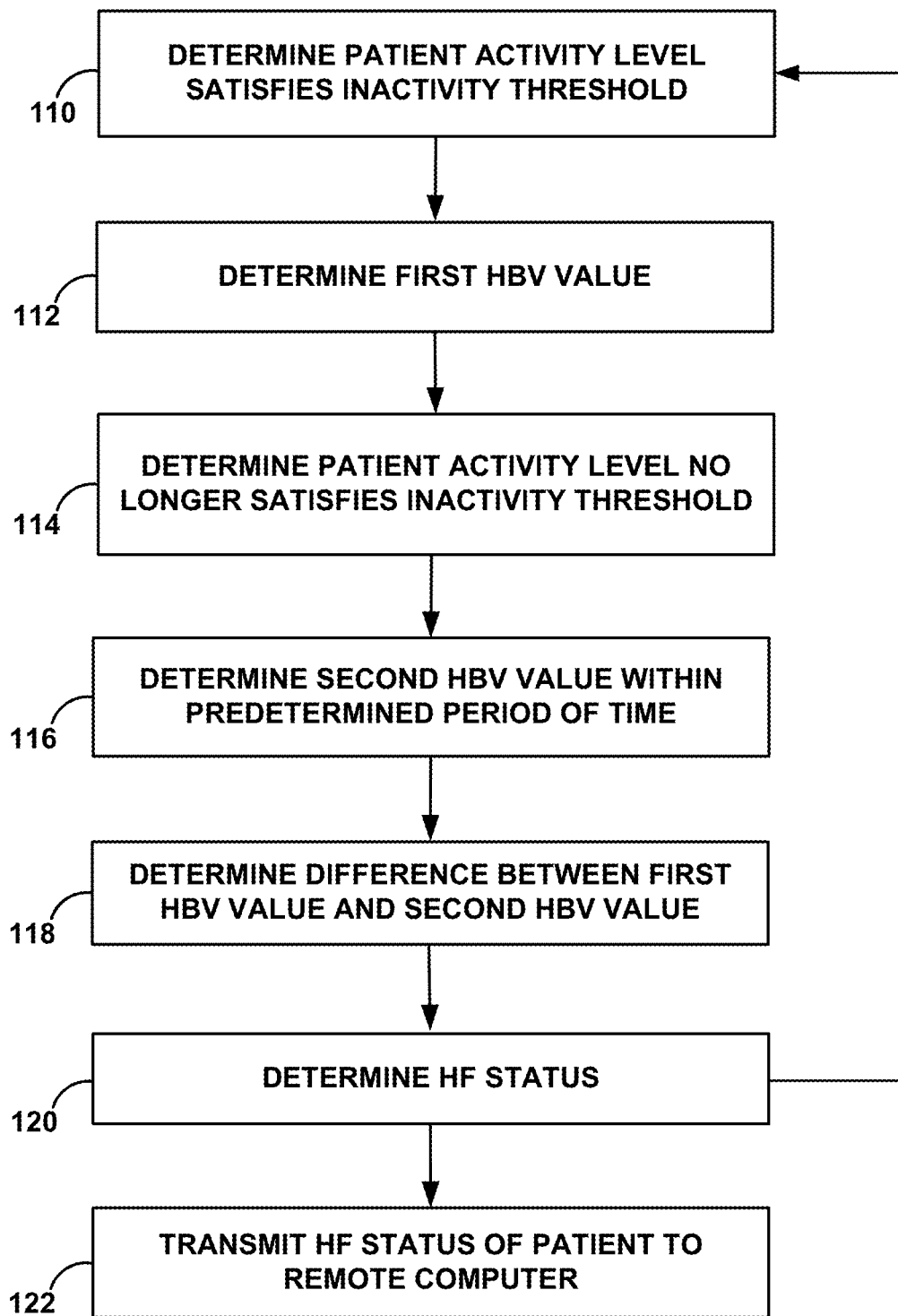
FIG. 6 is a flow diagram illustrating an example technique for determining a heart failure status of a patient based on a difference between a first value of at least one HBV metric of the patient and a second value of the at least one HBV metric of the patient and transmitting the heart failure status to a remote computer.
Figure 7:
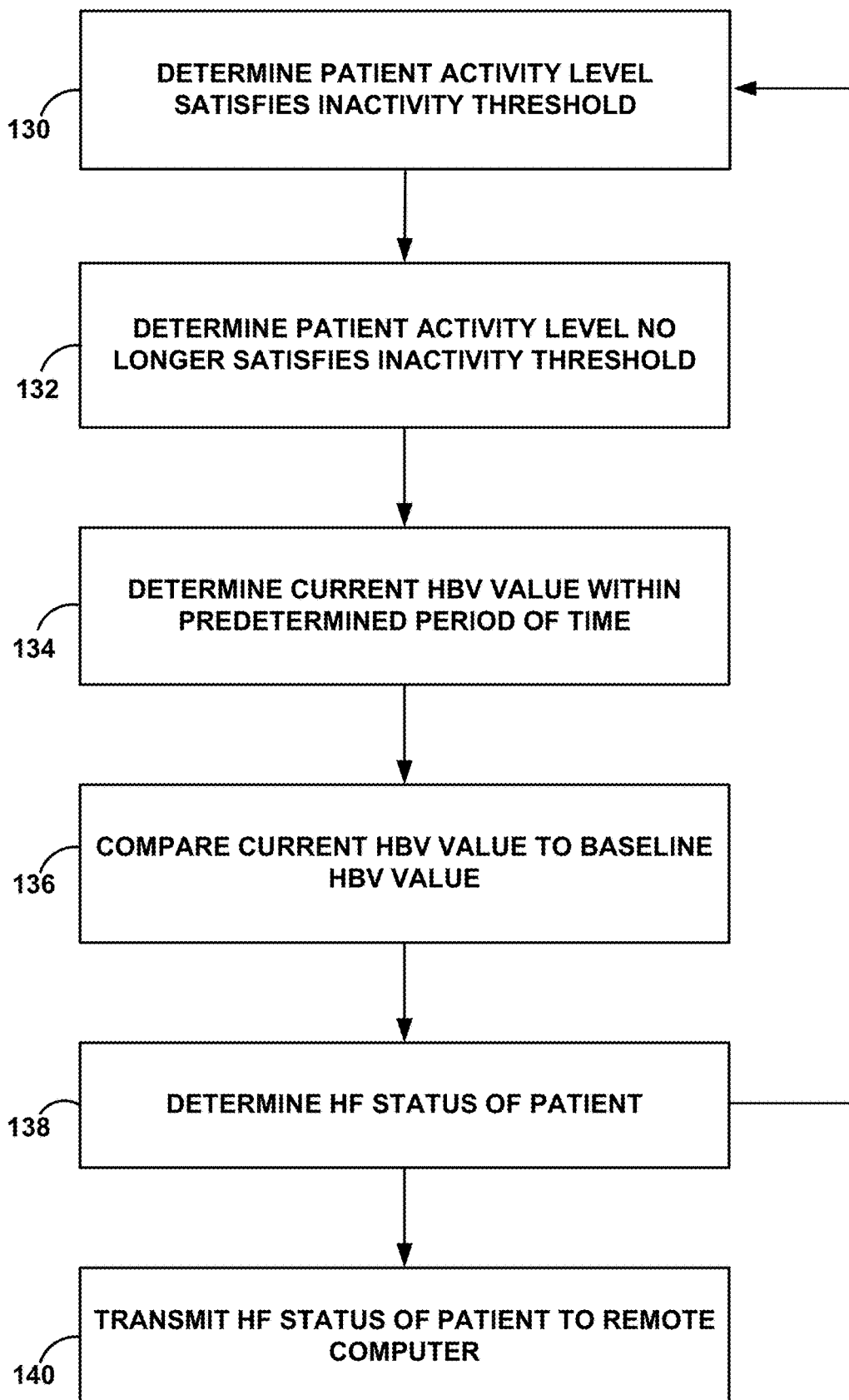
FIG. 7 is a flow diagram illustrating another example technique for determining a heart failure status of a patient based on a comparison of a current value of at least one HBV metric of the patient to a baseline value of the at least one HBV metric of the patient, and transmitting the heart failure status to a remote computer.
Figure 8:
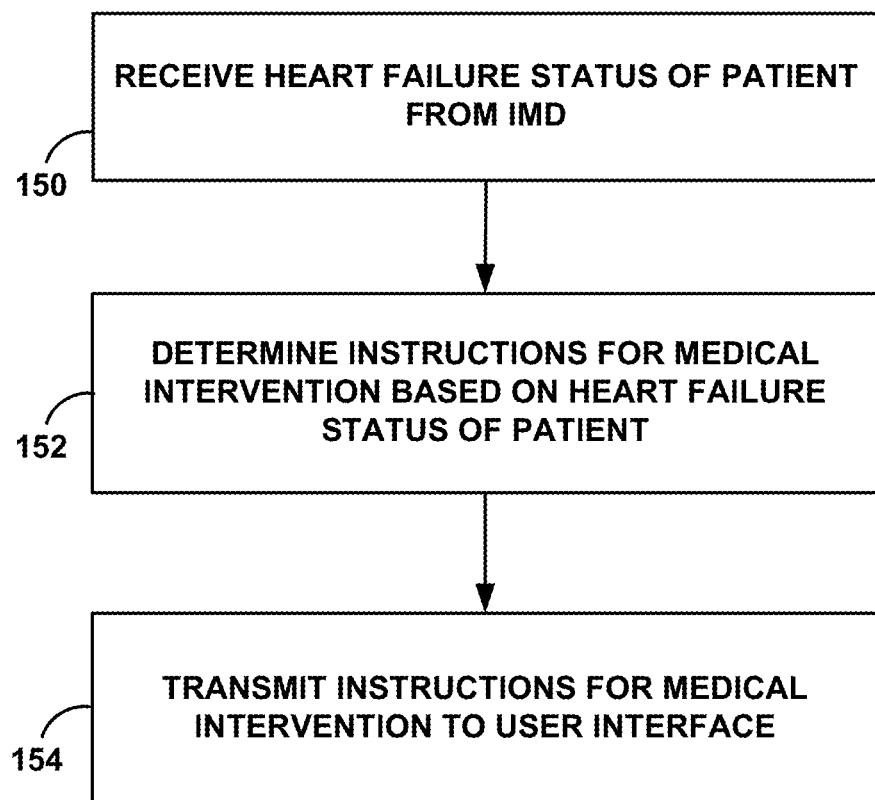
FIG. 8 is a flow diagram illustrating an example technique for a remote computer to determine instructions for a medical intervention based on a heart failure status of a patient received from the leadless implantable medical device of FIG. 1 and transmit the instructions to a user interface.

FIGS. 6-8 are flow diagrams illustrating various techniques related to determining a heart failure status of a patient based on a comparison of a difference between HBV values of the patient or a current HBV value of the patient to corresponding baseline values and transmitting instructions for medical intervention to a user interface. As described herein, the techniques illustrated FIGS. 6-8 may be employed using one or more components of medical device system 2, which have been described above with respect to FIGS. 1-5. Although described as being performed by processing circuitry 50 of IMD 10 for the sake of clarity, the techniques of FIGS. 6-8 may be performed, in whole or in part, by processing circuitry and memory of other devices of medical device system 2, as described herein. For example, one or more devices (e.g., external device 12 or other external device or server) or a clinician may, in some examples, carry out one or more steps attributed below to processing circuitry 50 of IMD 10.

FIG. 6 is a flow diagram illustrating an example technique for determining, by processing circuitry of medical device system 2 (e.g., processing circuitry 50 of IMD 10), a heart failure status of patient 4 based on a difference between a first value of at least one HBV metric of patient 4 and a second value of the at least one HBV metric of patient 4. The at least one HBV metric may be, for example, at least one of a T-wave alternans metric (e.g., a beat-to-beat variation in an amplitude or shape of a T-wave of a cardiac cycle), a PR duration metric (e.g., a beat-to-beat variability of a duration of a PR interval of a cardiac cycle), a short-term variability metric ((STV); which may quantify beat-to-beat variability in repolarization), or a phase-rectified signal averaging metric ((PRSA); which may characterize the capacity of heart 6 to decelerate or accelerate a cardiac rhythm and may be associated with cardiovascular risk).

According to the example of FIG. 6, processing circuitry 50 determines that an activity state of patient 4 satisfies at least one inactivity criterion based on at least one first signal received by processing circuitry 50 from sensors 58, such as from one or more accelerometers, one or more microphones, one or more pressure sensors, and/or one or more of electrodes 16A, 16B (110). The at least one inactivity criterion may be, in some examples, at least one of an activity level, posture, heart rate, or respiration rate of patient 4, or a time of day. In examples in which the at least one inactivity criterion includes a time of day, processing circuitry 50 may be configured to account for changes in time that may occur, such as when patient 4 travels from one time zone to another time zone and/or when daylight-savings time begins and/or ends. In some examples, the at least one inactivity criterion may be associated with patient 4 lying down and/or being asleep.

After determining that the activity state of patient 4 satisfies the at least one inactivity criterion, processing circuitry 50 then determines a first value of the at least one HBV metric of patient 4 while the activity state of patient 4 satisfies the at least one inactivity criterion, based on at least one second signal received by processing circuitry from sensors 58 such as from one or more accelerometers, one or more microphones, one or more pressure sensors, and/or one or more of electrodes 16A, 16B (112). For example, the at least one second signal may be a cardiac electrogram signal received by processing circuitry 50 from electrodes 16A and 16B or any other combination of at least two electrodes on IMD 10. In other examples, the at least one second signal may be received by processing circuitry 50 from one or more accelerometers, microphones, and/or pressure sensors and indicative of heart sounds associated with a heart rate of patient 4, on which basis processing circuitry 50 may determine the first value of the at least one HBV metric of patient 4. In any such examples, processing circuitry 50 may determine the first value of the at least one HBV metric of patient 4 by collecting a plurality of values of the at least one HBV metric during a measurement period. In some examples, such a measurement period may be a period of time encompassing a plurality of cardiac cycles of patient 4, such as 30 seconds, one minute, or any other suitable period of time. Processing circuitry 50 then may determine a difference between each value and a subsequent value collected during the measurement period and average or otherwise analyze the differences to determine the first value of the at least one HBV metric of patient 4.

After determining the first value of the at least one HBV metric, processing circuitry 50 then determines that the activity state of patient 4 no longer satisfies the at least one inactivity criterion based on the at least one first signal received by processing circuitry from sensors 58 (114). In examples in which the at least one inactivity criterion is associated with patient 4 lying down and/or being asleep, the determination that the activity state of patient 4 no longer satisfies the at least one inactivity criterion may comprise a determination that patient 4 is in an upright posture and/or has awakened from a sleep state. Processing circuitry 50 then determines, within a predetermined period of time after determining that the activity state of patient 4 no longer satisfies the at least one inactivity criterion, a second value of the at least one HBV metric while the activity state of patient 4 no longer satisfies the at least one inactivity criterion based on the at least one second signal (116). Processing circuitry 50 may determine the second value of the at least one HBV metric of patient 4 by collecting a plurality of values of the at least one HBV metric during a measurement period within the predetermined period of time. In some examples, such a measurement period may be a period of time encompassing a plurality of cardiac cycles of patient 4, such as 30 seconds, one minute, or any other suitable period of time. Processing 50 then may determine a difference between each value and a subsequent value collected during the measurement period and average or otherwise analyze the differences to determine the second value of the at least one HBV metric of patient 4.

Determining the first value of the at least one HBV metric while the activity state of patient 4 satisfies the at least one inactivity criterion and determining the second value of the at least one HBV metric while the activity state of patient 4 no longer satisfies the at least one inactivity criterion may enable processing circuitry 50 to identify changes in vascular tone of patient 4 that occur within the predetermined period of time after the activity state of patient 4 ceases to satisfy the at least one inactivity criterion. Changes in vascular tone of patient 4 during the predetermined period of time (e.g., about 30 minutes), which processing circuitry 50 may identify based on changes in values of the at least one HBV metric, may reflect changes in the balance between sympathetic activity and vagal tone of patient 4. As discussed above, changes in the balance between sympathetic activity and vagal tone of patient 4, occurring either during one activity cycle or across multiple activity cycles, may be associated with changes in a heart failure condition of patient 4. Thus, determining the second value of the at least one HBV metric during the predetermined period of time may help enable processing circuitry 50 to determine the heart failure status of patient 4.

In some examples, prior to determining that the activity state of patient 4 no longer satisfies the at least one inactivity criterion, processing circuitry 50 may determine that a period of time during which the activity state of patient 4 is expected to satisfy the at least one inactivity criterion, such as a time during which patient 4 is expected to be asleep has elapsed. Based on the determination that the period of time during which the activity state of patient 4 is expected to satisfy the at least one activity criterion has elapsed, processing circuitry 50 may increase a frequency at which an activity state and/or a value of the at least one HBV metric of patient 4 are determined in order to identify or approximate the time at which the activity state of patient 4 ceases to satisfy the at least one inactivity criterion. Identifying or approximating the time at which the activity state of patient 4 ceases to satisfy the at least one inactivity criterion may enable processing circuitry 50 to identify or approximate the beginning of the predetermined period of time and determine the second value of the at least one HBV metric within the predetermined period of time.

After determining the first and second values of the at least one HBV metric of patient 4, processing circuitry 50 determines a difference between the first and second values of the at least one HBV metric (118) and determines a heart failure status of patient 4 based on the difference (120). Processing circuitry 50 may determine the heart failure status of patient 4 by determining whether the difference between the first and second values of the at least one HBV metric satisfies an HBV difference threshold value associated with a change in the heart failure status of patient 4, which may be stored in baseline/threshold tables 64 of memory 56.

In some examples, processing circuitry 50 may periodically determine an updated value of the HBV difference threshold, which may enable processing circuitry 50 to track trends in the difference between the first and second values of the at least one HBV metric over multiple activity cycles of patient 4. The difference between the first and second values of the at least one HBV metric may correspond to a current activity cycle of patient 4. An activity cycle may include a period of time in which processing circuitry 50 both determines that the activity state of patient 4 satisfies the at least one inactivity criterion and determines that the activity state of patient 4 no longer satisfies the at least one inactivity criterion. Thus, in such examples, processing circuitry 50 may determine the HBV difference threshold value based on one or more values of the difference between the first and second values of the at least one HBV metric that correspond to one or more previous activity cycles of patient 4.

In some examples, an HBV difference threshold value may be an absolute value of a percentage of a baseline value of the difference between the first and second values of the at least one HBV metric, which may be a baseline value specific to patient 4. For example, if a baseline value of the difference between the first and second values of the at least one HBV metric=X, then an HBV difference threshold value may be X±0.2X. In other examples, the difference between the first and second values of the at least one HBV metric may be associated with multiple HBV difference threshold values that correspond to different percentages of the baseline value, thereby taking into account differences in significance between values that exceed a baseline value and values that are less than a baseline value. For example, if a baseline value of the difference between the first and second values of the at least one HBV metric=X, then HBV difference threshold values of the difference between the first and second values of the at least one HBV metric may be X+0.2X and X−0.1X. In such an example, values of the difference between the first and second values of the at least one HBV metric that are less than X, which may be associated with an already-advanced stage of a heart failure condition of patient 4, have relatively greater significance than values of that are greater than X, although the relative significance of difference values may be determined based on the individual patient. In any such examples, the threshold values may be based on deviations from corresponding baseline values, such as standard deviations or any other suitable statistical functions.

Processing circuitry 50 may repeat steps 110-120 to periodically determine updated heart failure statuses of patient 4 such as daily, weekly, monthly, or at any other suitable period. In some examples, the heart failure status of patient 4 may indicate a possibility that patient 4 may experience an adverse medical event within a certain period of time, such as a recurrence of symptoms, acute heart failure decompensation, or other adverse medical events that may require medical intervention such as hospitalization. Processing circuitry then transmits the health status of patient 4 to a remote computer, such as external device 12 (122). In some examples, processing circuitry 50 may transmit the heart failure status of patient 4 to the remote computer each time processing circuitry 50 determines the heart failure status of patient 4. In other examples, processing circuitry 50 may transmit the heart failure status of patient 4 to the remote computer less frequently, such as weekly or at any other suitable interval.

FIG. 7 is a flow diagram illustrating another example technique for determining, by processing circuitry of medical device system 2 (e.g., processing circuitry 50), a heart failure status of patient 4 based on a comparison of a value of at least one HBV metric of patient 4 to a baseline value of the at least one HBV metric, which may be stored in baseline/threshold tables 64 of memory 56. One or more aspects of the example technique illustrated in FIG. 7 may be substantially similar to one or more aspects of the example technique illustrated in FIG. 6. The example technique of FIG. 7 may differ from the example technique of FIG. 6 in that processing 50 may determine the heart failure status of patient 4 based on a difference between the current value of the at least one HBV metric, which may be determined while an activity state of patient 4 does not satisfy at least one inactivity criterion, and the baseline value of the at least one HBV metric, which also may be associated with a baseline activity state of patient 4 that does not satisfy the at least one inactivity criterion. Thus, the technique of FIG. 7 may be used, for example, to monitor changes in an absolute value of the at least one HBV metric occurring during a particular portion of an activity cycle of patient 4 over the course of multiple activity cycles. In contrast, in the example technique of FIG. 6, processing circuitry may determine the heart failure status of patient 4 based on the difference between first and second determined values of at least one HBV metric, which processing 50 respectively may determine when the activity state of patient 4 satisfies and no longer satisfies at least one inactivity criterion. Thus, the technique of FIG. 6 may be used, for example, to monitor changes in a difference between values of at least one HBV metric that occur during different portions of an activity cycle of patient 4 over the course of multiple activity cycles. In some instances, the example techniques of FIGS. 6 and 7 may be used to monitor different aspects of a heart failure status of patient 4.

According to the example of FIG. 7, processing circuitry 50 determines that an activity state of patient 4 satisfies at least one inactivity criterion based on at least one first signal received by processing circuitry 50 from sensors 58, such as from one or more accelerometers, one or more microphones, one or more pressure sensors, and/or one or more of electrodes 16A, 16B (130), such as in a manner substantially similar to that described above with respect to (110) of FIG. 6. After determining that the activity state of patient 4 satisfies the at least one inactivity criterion, processing 50 then determines that the activity state of patient 4 has increased by determining that the activity state of patient 4 no longer satisfies the at least one inactivity criterion based on the at least one first signal received by processing circuitry 50 from sensors 58 (132), such as in a manner substantially similar to that described above with respect to (114) of FIG. 6. In some examples in which the at least one inactivity criterion is associated with patient 4 lying down and/or being asleep, the determination that the activity state of patient 4 has increased may comprise a determination that patient 4 is in an upright posture and/or has awakened from a sleep state.

Processing circuitry 50 then determines, within a predetermined period of time after determining that the activity state of patient 4 has increased, a current value of the at least one HBV metric of patient 4 while the activity state of patient 4 no longer satisfies the at least one inactivity criterion based on the at least one second signal received from sensors 58 by processing circuitry 50 (134). In some examples, processing circuitry 50 may determine the current value of the at least one HBV metric of patient 4 in a manner substantially similar to the manner in which processing circuitry 50 may determine the second value of the at least one HBV metric of patient 4 as described above with respect to (116) of FIG. 6.

After determining the current value of the at least one HBV metric of patient 4, processing circuitry 50 compares the current value of the at least one HBV metric to the baseline value of the at least one HBV metric (136) and determines a heart failure status of patient 4 based on the difference (138). Processing circuitry 50 may determine the heart failure status of patient 4 by determining whether a difference between the current and baseline values of the at least one HBV metric satisfies an HBV threshold value associated with a change in the heart failure status of patient 4, which may be stored in baseline/threshold tables 64 of memory 56.

In some examples, processing circuitry 50 may periodically determine an updated value of the HBV threshold, such as in a manner similar to the manner in which processing circuitry 50 may determine updated values of the HBV difference threshold values described above with respect to FIG. 6, such as based on current values of the at least one HBV metric that correspond to one or more previous activity cycles of patient 4. Periodically determining updated values of the HBV threshold may enable processing circuitry 50 to track trends in the current value of the at least one HBV metric of patient 4 that occur during the same portion of an activity cycle of patient 4 (e.g., within about 30 minutes of an activity state of patient 4 increasing, such as upon awakening from a sleep state) over the course of multiple activity cycles.

As with steps 110-120 of the example of FIG. 6, processing circuitry 50 may repeat steps 130-138 to periodically determine updated heart failure statuses of patient 4 such as daily, weekly, monthly, or at any other suitable period. In some examples, the heart failure status of patient 4 may indicate a possibility that patient 4 may experience an adverse medical event within a certain period of time, such as a recurrence of symptoms, acute heart failure decompensation, or other adverse medical events that may require medical intervention such as hospitalization. Processing circuitry then transmits the health status of patient 4 to a remote computer, such as external device 12 (140). In some examples, processing circuitry 50 may transmit the heart failure status of patient 4 to the remote computer each time processing circuitry 50 determines the heart failure status of patient 4. In other examples, processing circuitry 50 may transmit the heart failure status of patient 4 to the remote computer less frequently, such as weekly or at any other suitable interval.

FIG. 8 is a flow diagram illustrating an example technique for a remote computer (e.g., external device 12) to determine instructions for a medical intervention based on a heart failure status of patient 4 received from IMD 10 and transmit the instructions to a user interface. The method illustrated in FIG. 8 may be used with any of the methods for determining a health status by IMD 10 described herein, such as the methods illustrated in FIGS. 6 and 7. In some examples, external device 12 is configured to receive a heart failure status of patient 4 from IMD 10, which may be transmitted to a processing circuitry of external device 12 via communication circuitry 54 and antenna 26 of IMD 10 (150). In some examples, the heart failure status of patient 4 may include a possibility that the patient will experience an adverse medical event, such as recurrent symptom(s), acute decompensation, hospitalization, or other adverse medical events.

In some examples, upon receiving the heart failure status of patient 4 from IMD 10 and prior to determining instructions for a medical intervention for patient 4, external device 12 may transmit one or more queries to a user device. For example, external device 12 may ask patient 4 or a caregiver to answer questions about recent or current activities or symptoms of patient 4, such as whether patient 4 recently has exercised, taken medications, or experienced symptoms. In addition, external device 12 may interrogate IMD 10 for recently-determined or current values of at least one HBV metric of patient 4, differences between first and second values of at least one HBV metric of patient 4, differences between current and baseline values of at least one HBV of patient 4, and/or heart-failure status determinations pertaining to patient 4, if IMD 10 did not already transmit such values, differences, and/or heart-failure status determinations to external device 12. Based on the heart failure status of patient 4, and optionally based on answers to queries and/or the current values of patient 4, external device 12 then may determine instructions for a medical intervention for patient 4 (152).

External device 12 may determine instructions for one or more medical interventions for patient 4 based on the heart failure status of patient 4. For example, external device 12 may determine instructions for modifying (e.g., start, stop, increase, or decrease) a dose of one or more drugs, such as diuretics, nitrates, beta-blockers, ivabradine, or inotropes. In some examples, instructions for medical interventions for patient 4 may take into account the presence of cardiac arrhythmia, as indicated by ECG signals of patient 4 detected by IMD 10. For example, instructions determined by external device 12 in the presence of arrhythmia may include instructions for patient 4 to avoid taking certain medications, instruct patient 4 to visit a healthcare facility, or may recommend starting CRT or changing CRT parameters.

In some examples, external device 12 may determine the instructions for medical intervention independent of clinician input, such as by selecting among treatment options stored in a memory of external device 12 or a centralized database that are associated with recently-determined or current values of at least one HBV metric of patient 4, differences between first and second values of at least one HBV metric of patient 4, differences between current and baseline values of at least one HBV of patient 4, and/or heart-failure status determinations pertaining to patient 4. In other examples, a clinician may determine the instructions for medical intervention on substantially the same basis, and input the instructions to external device 12. External device 12 then may transmit the instructions to an interface of the user device with patient 4 (154). In some examples, external device 12 may transmit follow-up queries to patient 4 or a caregiver via the user device after transmitting the instructions. Such queries may include questions pertaining to patient 4's understanding of the transmitted instructions, whether patient 4 has complied with the instructed medical intervention, and/or whether patient 4 is experiencing symptoms. External device 12 may store patient 4's responses in a memory of external device 12, or in a centralized database. A clinician may review the responses, and remotely follow-up with patient 4 as needed following any changes to patient 4's treatment for a heart failure condition. In this manner, the techniques and systems described herein advantageously may enable patient 4 to receive individualized, frequently updated treatment at less expense than a comparable number of clinician visits and/or hospitalizations would incur. In addition, the techniques and systems may help reduce recurrence of symptoms, acute decompensation events, and/or cardiac remodeling that may be caused by acute decompensation episodes, which in turn may help reduce or slow the progression of a heart failure condition of patient 4.

Although the example techniques for determining a heart failure status of a patient are described herein as being based on the parameter of HBV, such examples are not intended to be limiting. In some examples, a technique for determining a heart failure status of a patient may be based on one or more other parameters indicative of the heart failure status of the patient in combination with HBV. Examples of such other parameters, and techniques for determining heart failure status based on a plurality of parameters, are described in U.S. Patent Application Publication No. 2012/0253207 by Sarkar et al. and "Development and validation of an integrated diagnostic algorithm derived from parameters monitored in implantable devices for identifying patients at risk for heart failure hospitalization in an ambulatory setting" by Cowie et al., which are incorporated by reference herein in their entirety. Still other example parameters that may be used in such a technique for determining a heart failure status of a patient may include parameters such as edema (e.g., peripheral edema), pulse transit time, and/or other suitable parameters.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

The following examples are illustrative of the techniques described herein.

Example 1: A method for determining a heart failure status of a patient using a medical device comprising one or more sensors, the method comprising, by processing circuitry of a medical device system comprising the medical device: determining that an activity state of the patient satisfies at least one inactivity criterion based on at least one first signal received from the one or more sensors; determining a first value of at least one heart beat variability metric of the patient while the activity state of the patient satisfies the at least one inactivity criterion based on at least one second signal received from the one or more sensors;

determining, after determining the first value of the at least one heart beat variability metric, that the activity state of the patient no longer satisfies the at least one inactivity criterion based on the at least one first signal; determining, within a predetermined period of time after determining that the activity state of the patient no longer satisfies the at least one inactivity criterion, a second value of the at least one heart beat variability metric while the activity state of the patient no longer satisfies the at least one inactivity criterion based on the at least one second signal; determining a difference between the first value of the at least one heart beat variability metric and the second value of the at least one heart beat variability metric; and determining the heart failure status of the patient based on the difference.

Example 2: The method of example 1, wherein determining the heart failure status of the patient based on the difference between the first value of the at least one heart beat variability metric and the second value of the at least one heart beat variability metric beat variability comprises determining whether the difference between the first value of the at least one heart beat variability metric and the second value of the at least one heart beat variability metric satisfies a heart beat variability difference threshold value that is associated with a change in the heart failure status of the patient.

Example 3: The method of example 2, wherein the difference between the first value of the at least one heart beat variability metric and the second value of the at least one heart beat variability metric corresponds to a current activity cycle of the patient, an activity cycle comprising a period of time in which the processing circuitry both determines that the activity state of the patient satisfies the at least one inactivity criterion and determines that the activity state of the patient no longer satisfies the at least one inactivity criterion, wherein the heart beat variability difference threshold value is based on one or more values of the difference between the first value of the at least one heart beat variability metric and the second value of the at least one heart beat variability metric that correspond to one or more previous activity cycles of the patient.

Example 4: The method of example 2, wherein the at least one second signal is a current at least one second signal, the first value of the at least one heart beat variability metric is a current first value of the at least one heart beat variability metric, and the second value of the at least one heart beat variability metric is a current second value of the at least one heart beat variability metric, the method further comprising: receiving at least one baseline second signal from at least two of the plurality of electrodes that are the same as or different from the one or more sensors from which the processing circuitry receives the current at least one second signal; determining a baseline first value of the at least one heart beat variability metric and a baseline second value of the at least one heart beat variability metric based on the at least one baseline second signal; determining a baseline difference between the baseline first value of the at least one heart beat variability metric and the baseline second value of the at least one heart beat variability metric; and determining the heart beat variability difference threshold value based on the baseline difference between the baseline first value of the at least one heart beat variability metric and the baseline second value of the at least one heart beat variability metric.

Example 5: The method of any of examples 1 to 4, further comprising, by the processing circuitry: transmitting the heart failure status of the patient to a remote computer; receiving, from the remote computer, instructions for a medical intervention based on the heart failure status of the patient; and transmitting the instructions for the medical intervention to a user interface.

Example 6: The method of example 5, wherein the instructions for the medical intervention comprise at least one of a change in a drug selection, a change in a drug dosage, instructions to schedule a visit with a clinician, or instructions for the patient to seek medical attention.

Example 7: The method of any of examples 1 to 6, wherein determining the heart failure status of the patient based on the comparison comprises determining, by the processing circuitry, a possibility that the patient will experience an adverse medical event.

Example 8: The method of any of examples 1 to 7, wherein the at least one inactivity criterion comprises a value of least one of a patient activity level, a patient posture, a time of day, a patient heart rate, or a patient respiration rate.

Example 9: The method of any of examples 1 to 8, further comprising determining, prior to determining that the activity state of the patient no longer satisfies the at least one inactivity criterion, that a period of time during which the activity state of the patient is expected to satisfy the at least one inactivity criterion has elapsed.

Example 10: The method of any of examples 1 to 9, wherein determining that the activity state of the patient satisfies the at least one inactivity criterion comprises determining that the patient is lying down based on the at least one first signal, and wherein determining the first value of the at least one heart beat variability metric while the activity state of the patient satisfies the at least one inactivity criterion comprises determining the first value of the at least one heart beat variability metric while the patient is lying down.

Example 11: The method of example 10, wherein determining that the activity state of the patient no longer satisfies the at least one inactivity criterion comprises determining that the patient is in an upright posture based on the at least one first signal, and wherein determining the second value of the at least one heart beat variability metric while the activity level of the patient no longer satisfies the at least one inactivity criterion comprises determining the second value of the at least one heart beat variability metric while the patient is in the upright posture.

Example 12: The method of example 11, wherein determining that the patient is in the upright posture while the activity state of the patient no longer satisfies the at least one inactivity criterion after determining the first value of the at least one heart beat variability metric comprises determining that the patient has awakened from a sleep state, and wherein the predetermined period of time comprises a predetermined period of time after the patient has awakened from the sleep state.

Example 13: The method of example 12, wherein the predetermined period of time is a period of time occurring within about 30 minutes after the patient has awakened from the sleep state.

Example 14: The method of any of examples 1 to 13, wherein the first value of the at least one heart beat variability metric comprises a value of at least one sleeping heart beat variability metric and the second value of the at least one heart beat variability metric comprises a value of at least one waking heart beat variability metric, wherein determining that the activity state of the patient no longer satisfies the at least one inactivity criterion after determining the first value of the at least one heart beat variability metric comprises determining that the patient has awakened from a sleep state, and wherein the predetermined period of time comprises a predetermined period of time after the patient has awakened from the sleep state.

Example 15: The method of example 14, wherein the predetermined period of time is a period of time occurring within about 30 minutes after the patient has awakened from the sleep state.

Example 16: The method of any of examples 1 to 15, wherein determining the first value of the at least one heart beat variability metric comprises determining a representative first value of the at least one heart beat variability metric based on a plurality of first values of the at least one heart beat variability metrics determined while the activity state of the patient satisfies the at least one inactivity criterion.

Example 17: The method of any of examples 1 to 16, wherein the at least one heart beat variability metric comprises two or more heart beat variability metrics, wherein determining the first value of the at least one heart beat variability metric comprises determining a first value of each of the at least two heart beat variability metrics, and wherein determining the second value of the at least one heart beat variability metric comprises determining a second value of each of the at least two heart beat variability metrics.

Example 18: The method of any of examples 1 to 17, wherein the at least one heart beat variability metric comprises a corresponding at least one of a T-wave alternans metric, a PR duration metric, a short-term variability metric, or a phase-rectified signal averaging metric.

Example 19: The method of any of examples 1 to 18, wherein the at least one heart beat variability metric comprises at least one heart rate variability metric.

Example 20: The method of any of examples 1 to 19, wherein the first signal and the second signal comprise a common signal.

Example 21: The method of any of examples 1 to 20, wherein determining the second value of the at least one heart beat variability metric comprises determining a representative second value of the at least one heart beat variability metric based on a plurality of second values of the at least one heart beat variability metric determined during the predetermined period of time.

Example 22: The method of any of examples 1 to 21, further comprising determining an arrhythmia-prone status of the patient based on the difference.

Example 23: The method of any of examples 1 to 22, wherein the one or more sensors comprise a plurality of electrodes, and wherein the at least one second signal comprises a cardiac electrogram signal received from at least two of the plurality of electrodes.

Example 24: The method of any of examples 1 to 23, wherein the medical device is an implantable medical device configured for implantation within the patient.

Example 25: The method of example 24, wherein the implantable medical device comprises a housing configured for subcutaneous implantation, and wherein the one or more sensors are positioned on or within the housing.

Example 26: The method of example 24, wherein the implantable medical device comprises a leadless implantable medical device.

Example 27: A system for determining a heart failure status of a patient using a medical device, the system comprising: the medical device, wherein the medical device comprises one or more sensors; and processing circuitry. The processing circuitry is configured to: determine that an activity state of the patient satisfies at least one inactivity criterion based on at least one first signal received from the one or more sensors; determine a first value of at least one heart beat variability metric of the patient while the activity state of the patient satisfies the at least one inactivity criterion based on at least one second signal received from the one or more sensors; determine, after determining the first value of the at least one heart beat variability metric, that the activity state of the patient no longer satisfies the at least one inactivity criterion based on the at least one first signal; determine, within a predetermined period of time after determining that the activity state of the patient no longer satisfies the at least one inactivity criterion, a second value of the at least one heart beat variability metric while the activity state of the patient no longer satisfies the at least one inactivity criterion based on the at least one second signal; determine a difference between the first value of the at least one heart beat variability metric and the second value of the at least one heart beat variability metric; and determine the heart failure status of the patient based on the difference.

Example 28: The system of example 27, wherein the processing circuitry is configured to determine the heart failure status of the patient based on the difference between the first value of the at least one heart beat variability metric and the second value of the at least one heart beat variability metric to the baseline heart beat variability difference by at least determining whether the difference between the first value of the at least one heart beat variability metric and the second value of the at least one heart beat variability metric satisfies a heart beat variability difference threshold value that is associated with a change in the heart failure status of the patient.

Example 29: The system of example 28, wherein the difference between the first value of the at least one heart beat variability metric and the second value of the at least one heart beat variability metric corresponds to a current activity cycle of the patient, an activity cycle comprising a period of time in which the processing circuitry both determines that the activity state of the patient satisfies the at least one inactivity criterion and determines that the activity state of the patient no longer satisfies the at least one inactivity criterion, wherein the heart beat variability difference threshold value is based on one or more values of the difference between the first value of the at least one heart beat variability metric and the second value of the at least one heart beat variability metric that correspond to one or more previous activity cycles of the patient.

Example 30: The system of example 28, wherein the at least one second signal is a current at least one second signal, the first value of the at least one heart beat variability metric is a current first value of the at least one heart beat variability metric, and the second value of the at least one heart beat variability metric is a current second value of the at least one heart beat variability metric, wherein the processing circuitry is further configured to: receive at least one baseline second signal from at least two of the plurality of electrodes that are the same as or different from the one or more sensors from which the processing circuitry receives the current at least one second signal; determine a baseline first value of the at least one heart beat variability metric and a baseline second value of the at least one heart beat variability metric based on the at least one baseline second signal; determine a baseline difference between the baseline first value of the at least one heart beat variability metric and the baseline second value of the at least one heart beat variability metric; and determine the heart beat variability difference threshold value based on the difference between the baseline first value of the at least one heart beat variability metric and the baseline second value of the at least one heart beat variability metric.

Example 31: The system of any of examples 27 to 30, wherein the processing circuitry is further configured to: transmit the heart failure status of the patient to a remote computer; receive, from the remote computer, instructions for a medical intervention based on the heart failure status of the patient; and transmit the instructions for the medical intervention to a user interface.

Example 32: The system of example 31, wherein the instructions for the medical intervention comprise at least one of a change in a drug selection, a change in a drug dosage, instructions to schedule a visit with a clinician, or instructions for the patient to seek medical attention.

Example 33: The system of any of examples 27 to 32, wherein the processing circuitry is configured to determine the heart failure status of the patient based on the comparison by at least determining a possibility that the patient will experience an adverse medical event.

Example 34: The system of any of examples 27 to 33, wherein the at least one inactivity criterion comprises a value of least one of a patient activity level, a patient posture, a time of day, a patient heart rate, or a patient respiration rate.

Example 35: The system of any of examples 27 to 34, further comprising determining, prior to determining that the activity state of the patient no longer satisfies the at least one inactivity criterion, that a period of time during which the activity state of the patient is expected to satisfy the at least one inactivity criterion has elapsed.

Example 36: The system of any of examples 27 to 35, wherein the processing circuitry is configured to determine that the activity state of the patient satisfies the at least one inactivity criterion by at least determining that the patient is lying down based on the at least one first signal, and wherein the processing circuitry is configured to determine the first value of the at least one heart beat variability metric while the activity state of the patient satisfies the at least one inactivity criterion by at least determining the first value of the at least one heart beat variability metric while the patient is lying down.

Example 37: The system of example 36, wherein the processing circuitry is configured to determine that the activity state of the patient no longer satisfies the at least one inactivity criterion by at least determining that the patient is in an upright posture based on the at least one first signal, and wherein the processing circuitry is configured to determine the second value of the at least one heart beat variability metric while the activity level of the patient no longer satisfies the at least one inactivity criterion by at least determining the second value of the at least one heart beat variability metric while the patient is in the upright posture.

Example 38: The system of example 37, wherein the processing circuitry is configured to determine that the patient is in the upright posture while the activity state of the patient no longer satisfies the at least one inactivity criterion after determining the first value of the at least one heart beat variability metric by at least determining that the patient has awakened from a sleep state, and wherein the predetermined period of time comprises a predetermined period of time after the patient has awakened from the sleep state.

Example 39: The system of example 38, wherein the predetermined period of time is a period of time occurring within about 30 minutes after the patient has awakened from the sleep state.

Example 40: The system of any of examples 27 to 39, wherein the first value of the at least one heart beat variability metric comprises a value of at least one sleeping heart beat variability metric and the second value of the at least one heart beat variability metric comprises a value of at least one waking heart beat variability metric, wherein the processing circuitry is configured to determine that the activity state of the patient no longer satisfies the at least one inactivity criterion after determining the first value of the at least one heart beat variability metric comprises determining that the patient has awakened from a sleep state, and wherein the predetermined period of time comprises a predetermined period of time after the patient has awakened from the sleep state.

Example 41: The system of example 40, wherein the predetermined period of time is a period of time occurring within about 30 minutes after the patient has awakened from the sleep state.

Example 42: The system of any of examples 27 to 41, wherein the processing circuitry is configured to determine the first value of the at least one heart beat variability metric by at least determining a representative first value of the at least one heart beat variability metric based on a plurality of first values of the at least one heart beat variability metrics determined while the activity state of the patient satisfies the at least one inactivity criterion.

Example 43: The system of any of examples 27 to 42, wherein the at least one heart beat variability metric comprises two or more heart beat variability metrics, wherein the processing circuitry is configured to determine the first value of the at least one heart beat variability metric by at least determining a first value of each of the at least two heart beat variability metrics, and wherein the processing circuitry is configured to determine the second value of the at least one heart beat variability metric by at least determining a second value of each of the at least two heart beat variability metrics.

Example 44: The system of any of examples 27 to 43, wherein the at least one heart beat variability metric comprises a corresponding at least one of a T-wave alternans metric, a PR duration metric, a short-term variability metric, or a phase-rectified signal averaging metric.

Example 45: The system of any of examples 27 to 44, wherein the at least one heart beat variability metric comprises at least one heart rate variability metric.

Example 46: The system of any of examples 27 to 45, wherein the first signal and the second signal comprise a common signal.

Example 47: The system of any of examples 27 to 46, wherein the processing circuitry is configured to determine the second value of the at least one heart beat variability metric by at least determining a representative second value of the at least one heart beat variability metric based on a plurality of second values of the at least one heart beat variability metric determined during the predetermined period of time.

Example 48: The system of any of examples 27 to 47, wherein the processing circuitry is further configured to determine an arrhythmia-prone status of the patient based on the difference.

Example 49: The system of any examples 27 to 48, wherein the one or more sensors comprise a plurality of electrodes, and wherein the at least one second signal comprises a cardiac electrogram signal received from at least two of the plurality of electrodes.

Example 50: The system of any of examples 27 to 49, wherein the medical device is an implantable medical device configured for implantation within the patient.

Example 51: The system of example 50, wherein the implantable medical device comprises a housing configured for subcutaneous implantation, and wherein the one or more sensors are positioned on or within the housing.

Example 52: The system of example 50, wherein the implantable medical device comprises a leadless implantable medical device.

Example 53: A non-transitory computer-readable medium storing instructions for causing processing circuitry to perform a method for determining a heart failure status of a patient using a medical device comprising one or more sensors, the method comprising, by processing circuitry of a medical device system comprising the medical device: determining that an activity state of the patient satisfies at least one inactivity criterion based on at least one first signal received from the one or more sensors; determining a first value of at least one heart beat variability metric of the patient while the activity state of the patient satisfies the at least one inactivity criterion based on at least one second signal received from the one or more sensors; determining, after determining the first value of the at least one heart beat variability metric, that the activity state of the patient no longer satisfies the at least one inactivity criterion based on the at least one first signal; determining, within a predetermined period of time after determining that the activity state of the patient no longer satisfies the at least one inactivity criterion, a second value of the at least one heart beat variability metric while the activity state of the patient no longer satisfies the at least one inactivity criterion based on the at least one second signal; determining a difference between the first value of the at least one heart beat variability metric and the second value of the at least one heart beat variability metric; and determining the heart failure status of the patient based on the difference.

Example 54: The non-transitory computer-readable medium of example 53, wherein determining the heart failure status of the patient based on the difference between the first value of the at least one heart beat variability metric and the second value of the at least one heart beat variability metric to the baseline heart beat variability difference comprises determining whether the difference between the first value of the at least one heart beat variability metric and the second value of the at least one heart beat variability metric satisfies a heart beat variability difference threshold value that is associated with a change in the heart failure status of the patient.

Example 55: The non-transitory computer-readable medium of example 54, wherein the difference between the first value of the at least one heart beat variability metric and the second value of the at least one heart beat variability metric corresponds to a current activity cycle of the patient, an activity cycle comprising a period of time in which the processing circuitry both determines that the activity state of the patient satisfies the at least one inactivity criterion and determines that the activity state of the patient no longer satisfies the at least one inactivity criterion, wherein the heart beat variability difference threshold value is based on one or more values of the difference between the first value of the at least one heart beat variability metric and the second value of the at least one heart beat variability metric that correspond to one or more previous activity cycles of the patient.

Example 56: A method for determining a heart failure status of a patient using a medical device comprising one or more sensors, the method comprising, by processing circuitry of a medical device system comprising the medical device: determining that an activity state of the patient satisfies at least one inactivity criterion based on at least one first signal received from the one or more sensors; determining that the activity state of the patient has increased by determining that the activity state of the patient no longer satisfies the at least one inactivity criterion based on the at least one first signal after determining that the activity state of the patient satisfies the at least one inactivity criterion; determining, within a predetermined period of time after determining that the activity state of the patient has increased, a current value of at least one heart beat variability metric while the activity state of the patient no longer satisfies the at least one the inactivity criterion based on at least one second signal received from the one or more sensors; comparing the current value of the at least one heart beat variability metric to a baseline value of the at least one heart beat variability metric; and determining the heart failure status of the patient based on the comparison.

Example 57: The method of example 56, wherein comparing the current value of the at least one heart beat variability metric to the baseline value of the at least one heart beat variability metric comprises determining whether a difference between the current value of the at least one heart beat variability metric and the baseline value of the at least one heart beat variability metric satisfies at least one corresponding heart beat variability threshold value that is associated with a change in the heart failure status of the patient.

Example 58: The method of example 57, wherein the predetermined period of time is a current predetermined period of time, and wherein the at least one corresponding heart beat variability threshold value is based on one or more corresponding previous values of the at least one heart beat variability metric that correspond to one or more previous predetermined periods of time.

Example 59: The method of any of examples 56 to 58, further comprising, by the processing circuitry: transmitting the heart failure status of the patient to a remote computer; receiving, from the remote computer, instructions for a medical intervention based on the heart failure status of the patient; and transmitting the instructions for the medical intervention to a user interface.

Example 60: The method of any of examples 56 to 59, wherein determining the heart failure status of the patient based on the comparison comprises determining, by the processing circuitry, a possibility that the patient will experience an adverse medical event.

Example 61: The method of any of examples 56 to 60, wherein the at least one inactivity criterion comprises a value of least one of a patient activity level, a patient posture, a time of day, a patient heart rate, or a patient respiration rate.

Example 62: The method of any of examples 56 to 61, wherein determining that the activity state of the patient no longer satisfies the at least one inactivity criterion comprises determining that the patient is in an upright posture based on the at least one first signal, and wherein determining the current value of the at least one heart beat variability metric while the activity state of the patient no longer satisfies the at least one inactivity criterion comprises determining the current value of the at least one heart beat variability metric while the patient is in the upright posture.

Example 63: The method of example 62, wherein determining that the patient is in the upright posture and determining that the activity state of the patient has increased comprises determining that the patient has awakened from a sleep state, and wherein the predetermined period of time comprises a predetermined period of time after the patient has awakened from the sleep state.

Example 64: The method of example 63, wherein the predetermined period of time is a period of time occurring within about 30 minutes after the patient has awakened from the sleep state.

Example 65: The method of any of examples 56 to 64, wherein determining the current value of the at least one heart beat variability metric comprises determining a representative current value of the at least one heart beat variability metric based on a plurality of values of the at least one heart beat variability metric determined during the predetermined period of time.

Example 66: The method of any of examples 56 to 65, wherein the at least one heart beat variability metric comprises two or more heart beat variability metrics, and wherein determining the current value of the at least one heart beat variability metric comprises determining a current value of each of the at least two heart beat variability metrics.

Example 67: The method of any of examples 56 to 66, wherein the at least one heart beat variability metric comprises a corresponding at least one of a T-wave alternans metric, a PR duration metric, a short-term variability metric, or a phase-rectified signal averaging metric.

Example 68: The method of any of examples 56 to 67, wherein the at least one heart beat variability metric comprises at least one heart rate variability metric.

Example 69: The method of any of examples 56 to 68, wherein the baseline value of the at least one heart beat variability metric is a patient-specific baseline value of the at least one heart beat variability metric, and wherein the at least one second signal is at least one current second signal, the method further comprising: receiving at least one baseline second signal from the one or more sensors; and determining the patient-specific value of the at least one baseline heart beat variability metric based on the baseline at least one second signal.

Example 70: The method of any of examples 56 to 69, further comprising determining an arrhythmia-prone status of the patient based on the comparison.

Example 71: The method of any of examples 56 to 70, wherein the one or more sensors comprise a plurality of electrodes, and wherein the at least one second signal comprises a cardiac electrogram signal received from at least two of the plurality of electrodes.

Example 72: The method of any of examples 56 to 71, wherein the medical device is an implantable medical device configured for implantation within the patient Example 73: The method of example 72, wherein the implantable medical device comprises a housing configured for subcutaneous implantation, and wherein the one or more sensors are positioned on or within the housing.

Example 74: The method of example 72, wherein the implantable medical device comprises a leadless implantable medical device.

Example 75: A system for determining a heart failure status of a patient using a medical device, the system comprising: the medical device, wherein the medical device comprises one or more sensors; and processing circuitry. The processing circuitry is configured to: determine that an activity state of the patient satisfies at least one inactivity criterion based on at least one first signal received from the one or more sensors; determine that the activity state of the patient has increased by determining that the activity state of the patient no longer satisfies the at least one inactivity criterion based on the at least one first signal after determining that the activity state of the patient satisfies the at least one inactivity criterion; determine, within a predetermined period of time after determining that the activity state of the patient has increased, a current value of at least one heart beat variability metric while the activity state of the patient no longer satisfies the at least one the inactivity criterion based on at least one second signal received from the one or more sensors; compare the current value of the at least one heart beat variability metric to a baseline value of the at least one heart beat variability metric; and determine the heart failure status of the patient based on the comparison.

Example 76: The system of example 75, wherein the processing circuitry is configured to compare the current value of the at least one heart beat variability metric to the baseline value of the at least one heart beat variability metric by at least determining whether a difference between the current value of the at least one heart beat variability metric and the baseline value of the at least one heart beat variability metric satisfies at least one corresponding heart beat variability threshold value that is associated with a change in the heart failure status of the patient.

Example 77: The system of example 76, wherein the predetermined period of time is a current predetermined period of time, and wherein the at least one corresponding heart beat variability threshold value is based on one or more corresponding previous values of the at least one heart beat variability metric that correspond to one or more previous predetermined periods of time.

Example 78: The system of any of examples 75 to 77, wherein the processing circuitry is configured to: transmit the heart failure status of the patient to a remote computer; receiving, from the remote computer, instructions for a medical intervention based on the heart failure status of the patient; and transmit the instructions for the medical intervention to a user interface.

Example 79: The system of any of examples 75 to 78, wherein the processing circuitry is configured to determine the heart failure status of the patient based on the comparison by at least determining a possibility that the patient will experience an adverse medical event.

Example 80: The system of any of examples 75 to 79, wherein the at least one inactivity criterion comprises a value of least one of a patient activity level, a patient posture, a time of day, a patient heart rate, or a patient respiration rate.

Example 81: The system of any of examples 75 to 80, wherein the processing circuitry is configured to determine that the activity state of the patient no longer satisfies the at least one inactivity criterion by at least determining that the patient is in an upright posture based on the at least one first signal, and wherein the processing circuitry is configured to determine the current value of the at least one heart beat variability metric while the activity state of the patient no longer satisfies the at least one inactivity criterion by at least determining the current value of the at least one heart beat variability metric while the patient is in the upright posture.

Example 82: The system of example 81, wherein the processing circuitry is configured to determine that the patient is in the upright posture and determining that the activity state of the patient has increased by at least determining that the patient has awakened from a sleep state, and wherein the predetermined period of time comprises a predetermined period of time after the patient has awakened from the sleep state.

Example 83: The system of example 82, wherein the predetermined period of time is a period of time occurring within about 30 minutes after the patient has awakened from the sleep state.

Example 84: The system of any of examples 75 to 83, wherein the processing circuitry is configured to determine the current value of the at least one heart beat variability metric by at least determining a representative current value of the at least one heart beat variability metric based on a plurality of values of the at least one heart beat variability metric determined during the predetermined period of time.

Example 85: The system of any of examples 75 to 84, wherein the at least one heart beat variability metric comprises two or more heart beat variability metrics, and wherein the processing circuitry is configured to determine the current value of the at least one heart beat variability metric by at least determining a current value of each of the at least two heart beat variability metrics.

Example 86: The system of any of examples 75 to 85, wherein the at least one heart beat variability metric comprises a corresponding at least one of a T-wave alternans metric, a PR duration metric, a short-term variability metric, or a phase-rectified signal averaging metric.

Example 87: The system of any of examples 75 to 86, wherein the at least one heart beat variability metric comprises at least one heart rate variability metric.

Example 88: The system of any of examples 75 to 87, wherein the baseline value of the at least one heart beat variability metric is a patient-specific baseline value of the at least one heart beat variability metric, and wherein the at least one second signal is at least one current second signal, wherein the processing circuitry is further configured to: receive at least one baseline second signal from the one or more sensors; and determine the patient-specific value of the at least one baseline heart beat variability metric based on the baseline at least one second signal.

Example 89: The system of any of examples 75 to 88, wherein the processing circuitry is further configured to determine an arrhythmia-prone status of the patient based on the comparison.

Example 90: The system of any of examples 75 to 89, wherein the one or more sensors comprise a plurality of electrodes, and wherein the at least one second signal comprises a cardiac electrogram signal received from at least two of the plurality of electrodes.

Example 91: The system of any of examples 75 to 90, wherein the medical device is an implantable medical device configured for implantation within the patient.

Example 92: The system of example 91, wherein the implantable medical device comprises a housing configured for subcutaneous implantation, and wherein the one or more sensors are positioned on the housing.

Example 93: The system of example 91, wherein the implantable medical device comprises a leadless implantable medical device.

Example 94: A non-transitory computer-readable medium storing instructions for causing processing circuitry to perform a method for determining a heart failure status of a patient using a medical device comprising one or more sensors, the method comprising, by processing circuitry of a medical device system comprising the medical device: determining that an activity state of the patient satisfies at least one inactivity criterion based on at least one first signal received from the one or more sensors; determining that the activity state of the patient has increased by determining that the activity state of the patient no longer satisfies the at least one inactivity criterion based on the at least one first signal after determining that the activity state of the patient satisfies the at least one inactivity criterion; determining, within a predetermined period of time after determining that the activity state of the patient has increased, a current value of at least one heart beat variability metric while the activity state of the patient no longer satisfies the at least one the inactivity criterion based on at least one second signal received from the one or more sensors; comparing the current value of the at least one heart beat variability metric to a baseline value of the at least one heart beat variability metric; and determining the heart failure status of the patient based on the comparison.

Example 95: The non-transitory computer-readable medium of example 94, wherein comparing the current value of the at least one heart beat variability metric to the baseline value of the at least one heart beat variability metric comprises determining whether a difference between the current value of the at least one heart beat variability metric and the baseline value of the at least one heart beat variability metric satisfies at least one corresponding heart beat variability threshold value that is associated with a change in the heart failure status of the patient.

Various aspects of the disclosure have been described. These and other aspects are within the scope of the following claims.

What is claimed is:

1. A system for determining a heart failure status of a patient using a medical device, the system comprising:
the medical device, wherein the medical device comprises one or more sensors; and
processing circuitry configured to:
determine that an activity state of the patient satisfies at least one inactivity criterion based on at least one first signal received from the one or more sensors;
determine a first value of at least one heart beat variability metric of the patient while the activity state of the patient satisfies the at least one inactivity criterion based on at least one second signal received from the one or more sensors;
determine, after determining the first value of the at least one heart beat variability metric, that the activity state of the patient no longer satisfies the at least one inactivity criterion based on the at least one first signal;
determine, in response to and within a predetermined period of time after determining that the activity state of the patient no longer satisfies the at least one inactivity criterion, a second value of the at least one heart beat variability metric while the activity state of the patient no longer satisfies the at least one inactivity criterion based on the at least one second signal, the predetermined period of time being less than thirty minutes;
determine a difference between the first value of the at least one heart beat variability metric and the second value of the at least one heart beat variability metric; and
generate the heart failure status of the patient, based on the difference, to be output to a remote computer to determine instructions for medical intervention based on the heart failure status.

2. The system of claim 1, wherein the processing circuitry is configured to generate the heart failure status of the patient based on the difference between the first value of the at least one heart beat variability metric and the second value of the at least one heart beat variability metric by at least determining whether the difference between the first value of the at least one heart beat variability metric and the second value of the at least one heart beat variability metric satisfies a heart beat variability difference threshold value that is associated with a change in the heart failure status of the patient.

3. The system of claim 2, wherein the at least one second signal is a current at least one second signal, the first value of the at least one heart beat variability metric is a current first value of the at least one heart beat variability metric, and the second value of the at least one heart beat variability metric is a current second value of the at least one heart beat variability metric, wherein the processing circuitry is further configured to:
receive at least one baseline second signal from at least two of a plurality of electrodes that are the same as or different from the one or more sensors from which the processing circuitry receives the current at least one second signal;
determine a baseline first value of the at least one heart beat variability metric and a baseline second value of the at least one heart beat variability metric based on the at least one baseline second signal;
determine a baseline difference between the baseline first value of the at least one heart beat variability metric and the baseline second value of the at least one heart beat variability metric; and
determine the heart beat variability difference threshold value based on the difference between the baseline first value of the at least one heart beat variability metric and the baseline second value of the at least one heart beat variability metric.

4. The system of claim 1, wherein the processing circuitry is further configured to:
transmit the heart failure status of the patient to the remote computer;
receive, from the remote computer, instructions for medical intervention based on the heart failure status of the patient; and
transmit the instructions for medical intervention to a user interface.

5. The system of claim 1, wherein the processing circuitry is configured to generate the heart failure status of the patient based on the difference by at least determining a possibility that the patient will experience an adverse medical event.

6. The system of claim 1, wherein the at least one inactivity criterion comprises a value of least one of a patient activity level, a patient posture, a time of day, a patient heart rate, or a patient respiration rate.

7. The system of claim 1, wherein the processing circuitry is configured to determine, prior to determining that the activity state of the patient no longer satisfies the at least one inactivity criterion, that a period of time during which the activity state of the patient is expected to satisfy the at least one inactivity criterion has elapsed.

8. The system of claim 1, wherein the processing circuitry is configured to:
determine that the activity state of the patient satisfies the at least one inactivity criterion by at least determining that the patient is lying down based on the at least one first signal;
determine the first value of the at least one heart beat variability metric while the activity state of the patient satisfies the at least one inactivity criterion by at least determining the first value of the at least one heart beat variability metric while the patient is lying down; and
determine that the activity state of the patient no longer satisfies the at least one inactivity criterion by at least determining that the patient is in an upright posture based on the at least one first signal, and wherein the processing circuitry is configured to determine the second value of the at least one heart beat variability metric while the activity level of the patient no longer satisfies the at least one inactivity criterion by at least determining the second value of the at least one heart beat variability metric while the patient is in the upright posture.

9. The system of claim 1, wherein the first value of the at least one heart beat variability metric comprises a value of at least one sleeping heart beat variability metric and the second value of the at least one heart beat variability metric comprises a value of at least one waking heart beat variability metric, wherein the processing circuitry is configured to determine that the activity state of the patient no longer satisfies the at least one inactivity criterion after determining the first value of the at least one heart beat variability metric comprises determining that the patient has awakened from a sleep state, and wherein the predetermined period of time comprises a predetermined period of time after the patient has awakened from the sleep state.

10. The system of claim 1, wherein the at least one heart beat variability metric comprises a corresponding at least one of a T-wave alternans metric, a PR duration metric, a short-term variability metric, or a phase-rectified signal averaging metric.

11. The system of claim 1, wherein the at least one heart beat variability metric comprises at least one heart rate variability metric.

12. The system of claim 1, wherein the medical device is an implantable medical device configured for implantation within the patient.

13. The system of claim 12, wherein the implantable medical device comprises a housing configured for subcutaneous implantation, and wherein the one or more sensors are positioned on or within the housing.

14. The system of claim 12, wherein the implantable medical device comprises a leadless implantable medical device.

15. A system for determining a heart failure status of a patient using a medical device, the system comprising:
the medical device, wherein the medical device comprises one or more sensors; and
processing circuitry configured to:
determine that an activity state of the patient satisfies at least one inactivity criterion based on at least one first signal received from the one or more sensors;
determine a first value of at least one heart beat variability metric of the patient while the activity state of the patient satisfies the at least one inactivity criterion based on at least one second signal received from the one or more sensors;
determine, after determining the first value of the at least one heart beat variability metric, that the activity state of the patient no longer satisfies the at least one inactivity criterion based on the at least one first signal;
determine, in response to and within a predetermined period of time after determining that the activity state of the patient no longer satisfies the at least one inactivity criterion, a second value of the at least one heart beat variability metric while the activity state of the patient no longer satisfies the at least one inactivity criterion based on the at least one second signal;

determine a difference between the first value of the at least one heart beat variability metric and the second value of the at least one heart beat variability metric; and generate the heart failure status of the patient, by at least determining whether the difference between the first value of the at least one heart beat variability metric and the second value of the at least one heart beat variability metric satisfies a heart beat variability difference threshold value that is associated with a change in the heart failure status of the patient, to be output to a remote computer to determine instructions for medical intervention based on the heart failure status, wherein the difference between the first value of the at least one heart beat variability metric and the second value of the at least one heart beat variability metric corresponds to a current activity cycle of the patient, an activity cycle comprising a period of time in which the processing circuitry both determines that the activity state of the patient satisfies the at least one inactivity criterion and determines that the activity state of the patient no longer satisfies the at least one inactivity criterion, wherein the heart beat variability difference threshold value is based on one or more values of the difference between the first value of the at least one heart beat variability metric and the second value of the at least one heart beat variability metric that correspond to one or more previous activity cycles of the patient.

16. A non-transitory computer-readable medium storing instructions for causing processing circuitry to perform a method for determining a heart failure status of a patient using a medical device comprising one or more sensors, the method comprising, by processing circuitry of a medical device system comprising the medical device:

determining that an activity state of the patient satisfies at least one inactivity criterion based on at least one first signal received from the one or more sensors;

determining a first value of at least one heart beat variability metric of the patient while the activity state of the patient satisfies the at least one inactivity criterion based on at least one second signal received from the one or more sensors;

determining, after determining the first value of the at least one heart beat variability metric, that the activity state of the patient no longer satisfies the at least one inactivity criterion based on the at least one first signal;

determining, in response to and within a predetermined period of time after determining that the activity state of the patient no longer satisfies the at least one inactivity criterion, a second value of the at least one heart beat variability metric while the activity state of the patient no longer satisfies the at least one inactivity criterion based on the at least one second signal, the predetermined period of time being less than thirty minutes;

determining a difference between the first value of the at least one heart beat variability metric and the second value of the at least one heart beat variability metric; and generating the heart failure status of the patient, based on the difference, to be output to a remote computer to determine instructions for medical intervention based on the heart failure status.

17. A system for determining a heart failure status of a patient using a medical device, the system comprising:

the medical device, wherein the medical device comprises one or more sensors; and processing circuitry configured to:

determine that an activity state of the patient satisfies at least one inactivity criterion based on at least one first signal received from the one or more sensors;

determine that the activity state of the patient has increased by determining that the activity state of the patient no longer satisfies the at least one inactivity criterion based on the at least one first signal after determining that the activity state of the patient satisfies the at least one inactivity criterion;

determine, in response to and within a predetermined period of time after determining that the activity state of the patient has increased, a current value of at least one heart beat variability metric while the activity state of the patient no longer satisfies the at least one the inactivity criterion based on at least one second signal received from the one or more sensors, the predetermined period of time being less than thirty minutes;

compare the current value of the at least one heart beat variability metric to a baseline value of the at least one heart beat variability metric; and generate the heart failure status of the patient, based on the comparison, to be output to a remote computer to determine instructions for medical intervention based on the heart failure status.

18. An implantable medical device comprising:
one or more sensors; and
processing circuitry configured to:

determine that an activity state of the patient satisfies at least one inactivity criterion based on at least one first signal received from the one or more sensors;

determine a first value of at least one heart beat variability metric of the patient while the activity state of the patient satisfies the at least one inactivity criterion based on at least one second signal received from the one or more sensors;

determine, after determining the first value of the at least one heart beat variability metric, that the activity state of the patient no longer satisfies the at least one inactivity criterion based on the at least one first signal;

determine, in response to and within a predetermined period of time after determining that the activity state of the patient no longer satisfies the at least one inactivity criterion, a second value of the at least one heart beat variability metric while the activity state of the patient no longer satisfies the at least one inactivity criterion based on the at least one second signal, the predetermined period of time being less than thirty minutes;

determine a difference between the first value of the at least one heart beat variability metric and the second value of the at least one heart beat variability metric; and generate the heart failure status of the patient, based on the difference, to be output to a remote computer to determine instructions for medical intervention based on the heart failure status.

19. The device of claim 18, wherein the processing circuitry is configured to generate the heart failure status of the patient based on the difference between the first value of the at least one heart beat variability metric and the second value of the at least one heart beat variability metric by at least determining whether the difference between the first value of the at least one heart beat variability metric and the second value of the at least one heart beat variability metric satisfies a heart beat variability difference threshold value that is associated with a change in the heart failure status of the patient.

20. The device of claim 19, wherein the at least one second signal is a current at least one second signal, the first value of the at least one heart beat variability metric is a current first value of the at least one heart beat variability metric, and the second value of the at least one heart beat variability metric is a current second value of the at least one heart beat variability metric, wherein the processing circuitry is further configured to:
receive at least one baseline second signal from at least two of a plurality of electrodes that are the same as or different from the one or more sensors from which the processing circuitry receives the current at least one second signal;
determine a baseline first value of the at least one heart beat variability metric and a baseline second value of the at least one heart beat variability metric based on the at least one baseline second signal;
determine a baseline difference between the baseline first value of the at least one heart beat variability metric and the baseline second value of the at least one heart beat variability metric; and
determine the heart beat variability difference threshold value based on the difference between the baseline first value of the at least one heart beat variability metric and the baseline second value of the at least one heart beat variability metric.

21. The device of claim 18, wherein the processing circuitry is further configured to:
transmit the heart failure status of the patient to the remote computer;
receive, from the remote computer, the instructions for medical intervention based on the heart failure status of the patient; and
transmit the instructions for medical intervention to a user interface.

22. The device of claim 18, wherein the processing circuitry is configured to determine the heart failure status of the patient based on the difference by at least determining a possibility that the patient will experience an adverse medical event.

23. The device of claim 18, wherein the at least one inactivity criterion comprises a value of least one of a patient activity level, a patient posture, a time of day, a patient heart rate, or a patient respiration rate.

24. The device of claim 18, wherein the processing circuitry is configured to determine, prior to determining that the activity state of the patient no longer satisfies the at least one inactivity criterion, that a period of time during which the activity state of the patient is expected to satisfy the at least one inactivity criterion has elapsed.

25. The device of claim 18, wherein the processing circuitry is configured to:
determine that the activity state of the patient satisfies the at least one inactivity criterion by at least determining that the patient is lying down based on the at least one first signal;
determine the first value of the at least one heart beat variability metric while the activity state of the patient satisfies the at least one inactivity criterion by at least determining the first value of the at least one heart beat variability metric while the patient is lying down; and determine that the activity state of the patient no longer satisfies the at least one inactivity criterion by at least determining that the patient is in an upright posture based on the at least one first signal, and wherein the processing circuitry is configured to determine the second value of the at least one heart beat variability metric while the activity level of the patient no longer satisfies the at least one inactivity criterion by at least determining the second value of the at least one heart beat variability metric while the patient is in the upright posture.

26. The device of claim 18, wherein the first value of the at least one heart beat variability metric comprises a value of at least one sleeping heart beat variability metric and the second value of the at least one heart beat variability metric comprises a value of at least one waking heart beat variability metric, wherein the processing circuitry is configured to determine that the activity state of the patient no longer satisfies the at least one inactivity criterion after determining the first value of the at least one heart beat variability metric comprises determining that the patient has awakened from a sleep state, and wherein the predetermined period of time comprises a predetermined period of time after the patient has awakened from the sleep state.

27. The device of claim 18, wherein the at least one heart beat variability metric comprises a corresponding at least one of a T-wave alternans metric, a PR duration metric, a short-term variability metric, or a phase-rectified signal averaging metric.

28. The device of claim 18, wherein the at least one heart beat variability metric comprises at least one heart rate variability metric.

29. The device of claim 18 further comprising:
a housing configured for subcutaneous implantation, wherein the one or more sensors are positioned on or within the housing.

30. The device of claim 18, wherein the implantable medical device comprises a leadless implantable medical device.

31. An implantable medical device comprising:
one or more sensors; and
processing circuitry configured to:
determine that an activity state of the patient satisfies at least one inactivity criterion based on at least one first signal received from the one or more sensors;
determine a first value of at least one heart beat variability metric of the patient while the activity state of the patient satisfies the at least one inactivity criterion based on at least one second signal received from the one or more sensors;
determine, after determining the first value of the at least one heart beat variability metric, that the activity state of the patient no longer satisfies the at least one inactivity criterion based on the at least one first signal;
determine, in response to and within a predetermined period of time after determining that the activity state of the patient no longer satisfies the at least one inactivity criterion, a second value of the at least one heart beat variability metric while the activity state of the patient no longer satisfies the at least one inactivity criterion based on the at least one second signal;
determine a difference between the first value of the at least one heart beat variability metric and the second value of the at least one heart beat variability metric; and generate the heart failure status of the patient, by at least determining whether the difference between the first value of the at least one heart beat variability metric and the second value of the at least one heart beat variability metric satisfies a heart beat variability difference threshold value that is associated with a change in the heart failure status of the patient, to be output to a remote computer to determine instructions for medical intervention based on the heart failure status, wherein the difference between the first value of the at least one heart beat variability metric and the second value of the at least one heart beat variability metric corresponds to a current activity cycle of the patient, an activity cycle comprising a period of time in which the processing circuitry both determines that the activity state of the patient satisfies the at least one inactivity criterion and determines that the activity state of the patient no longer satisfies the at least one inactivity criterion, wherein the heart beat variability difference threshold value is based on one or more values of the difference between the first value of the at least one heart beat variability metric and the second value of the at least one heart beat variability metric that correspond to one or more previous activity cycles of the patient.

\* \* \* \* \*